United States Patent [19]

Inoue et al.

[11] Patent Number: 4,778,912
[45] Date of Patent: Oct. 18, 1988

[54] PHOSPHOLIPID DERIVATIVES

[75] Inventors: Keizo Inoue, Tokyo; Hiroaki Normura; Tetsuya Okutani, both of Osaka, all of Japan

[73] Assignee: Takeda Chemical Industries, Ltd., Osaka, Japan

[21] Appl. No.: 933,210

[22] Filed: Nov. 21, 1986

[30] Foreign Application Priority Data

Nov. 29, 1985 [JP] Japan .................................. 60-269889

[51] Int. Cl.$^4$ .............................................. C07F 9/10
[52] U.S. Cl. .................................... 558/170; 558/169
[58] Field of Search ................................. 558/169, 170

[56] References Cited

U.S. PATENT DOCUMENTS

| | | | |
|---|---|---|---|
| 4,159,988 | 7/1979 | Eibl et al. ............................ | 558/169 |
| 4,382,035 | 5/1983 | Eibl .................................... | 260/403 |
| 4,426,330 | 1/1984 | Sears .................................. | 260/403 |
| 4,534,899 | 8/1985 | Sears .................................. | 260/403 |
| 4,640,913 | 2/1987 | Wissner et al. ...................... | 558/169 |

FOREIGN PATENT DOCUMENTS 0099068 1/1984 European Pat. Off. .
84/00367 2/1984 World Int. Prop. O. .

OTHER PUBLICATIONS

Tokumura et al., J. Biol. Chem., vol. 260, No. 23, 1985, pp. 12710–12714.
Wissner et al., J. Med. Chem., vol. 29, No. 3, 1986, pp. 328–333.

*Primary Examiner*—Anton H. Sutto
*Attorney, Agent, or Firm*—Wegner & Bretschneider

[57] ABSTRACT

Phospholipid derivatives of the formula:

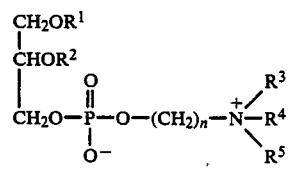

wherein $R^1$ is a higher alkyl, acylmethyl or alkylcarbamoyl group which may be substituted by cycloalkyl; $R^2$ is a lower alkyl which may be substituted by carboxy, formyl or lower acyl, a carbamoyl or thiocarbamoyl group which is substituted by lower alkyl, or an acetoacetyl group; $R^3$, $R^4$ and $R^5$ are independently hydrogen or lower alkyl, or

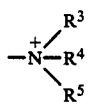

represents a cyclic ammonio group; and n represents an integer of 8 to 14, and salts thereof have antitumor activity.

12 Claims, No Drawings

PHOSPHOLIPID DERIVATIVES

FIELD OF THE INDUSTRIAL APPLICATION

This invention relates to phospholipid derivatives useful as antitumor agents. More particularly, this invention provides compounds of the formula:

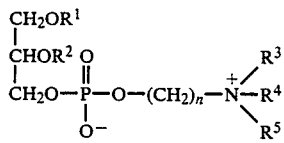

wherein $R^1$ is a higher alkyl, higher acylmethyl or higher alkylcarbamoyl group which may be substituted by cycloalkyl, $R^2$ is a lower alkyl group which may be substituted by carboxy, formyl or lower acyl, or a carbamoyl or thiocarbamoyl group substituted by lower alkyl or an acetoacetyl group; $R^3$, $R^4$ and $R^5$ are independently hydrogen or lower alkyl, or

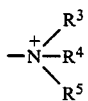

represents a cyclic ammonio group; and n represents an integer of 8 to 14, or salts thereof.

DESCRIPTION OF THE PRIOR ART

It has recently been made known that a platelet activating factor (hereinafter referred to as PAF) exists in the organism of various animals including human, as a phospholipid derivative represented by the formula:

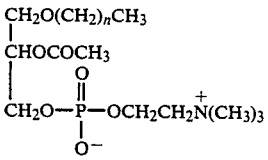

wherein n represents 15 or 17. The compound of the formula (II) is known to possess neutrophil-activating, tissue-impairing, vessel-permeability enhancing, blood-pressure lowering, heart function inhibiting, bronchoconstrictor and other actions, together with a strong platelet aggregation action. Its toxicity for warm-blooded animals is very high and it is recognized, for example, that a fatal dose for a mouse is about 50 mg/kg (iv administration).

Also, synthetic phospholipid compounds similar to the aforesaid compound (II) are known to have actions similar to those of PAF, although to a greater or lesser extent depending upon their difference in the structure.

On the other hand, as a natural phosphatidylcholine derivative, there is known a synthetic phospholipid compound represented by the following formula:

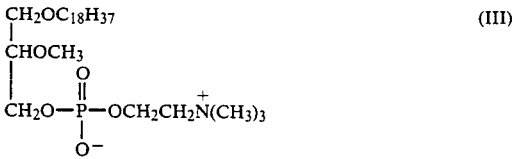

(For example, the gazette of Japanese Unexamined Patent Publication No. 134027/1977.) The above described compound (III) is known to exhibit an antitumor action unlike natural phospholipid compounds. In addition, This compound (III) is also known to possess a platelet activating action. [D. J. Hanahan et al.: Biochemical and Biophysical Research Communications 99, 183 (1981)] This kind of action is likely to cause serious circulatory disorders such as thrombosis and angina pectoris. Also, both blood-pressure lowering and topically irritating actions are observed for the compound (III), and these actions all constitute side effects. The high degree of its toxicity is known. [W. E. Berdel et al.: Anticancer Research 1, 345 (1981)] Consequently, its utilization as a pharmaceutical is restricted.

In Thrombosis Research, 30, 143 (1983), there is described a phospholipid compound of the formula:

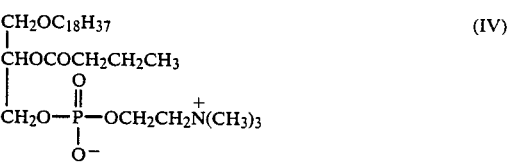

The above-mentioned compound also shows a platelet activating action (about 1/10 activity of that of PAF (II)).

Furthermore, as phospholipid compounds having a structure similar to that of the compound represented by the formula (I) of the present invention, there are some compounds, which are included in the claim mentioned in the gazette of Japanese Unexamined Patent Publication No. 192825/1983, but it is known that a compound of the following formula (V) wherein a substituent having a carbonyl group is introduced into the 2-position, for example, possesses remarkably strong platelet activating activity.

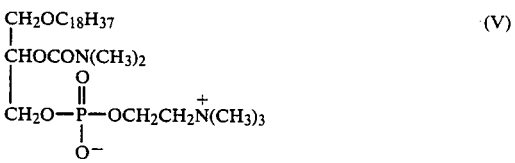

[H. Hayashi et al: Journal of Biochemistry 97, 1737 (1985)] Therefore, the use of the compound (V) as a pharmaceutical is restricted similar to the case of the aforementioned compounds.

As mentioned above, synthetic phospholipid compounds having a relatively small substituent at the 2-position have a PAF-like action and some problems remain for its use as a drug for the aforementioned reasons.

Also, the gazette of Japanese Unexamined Patent Publication No. 35194/1983 teaches a compound represented by the following formula:

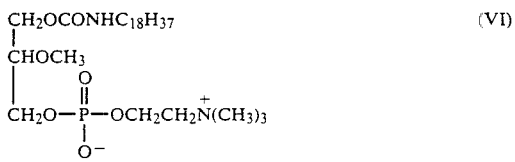

The antitumor effect of the above compound, however, is not sufficient.

Synthetic phospholipid compounds, particularly those which have a relatively small substituent at 2-position, generally possess actions such as platelet aggregating and blood-pressure lowering actions, as mentioned above. Since such actions constitute side effects in utilizing the synthetic phospholipid compound as an antitumor agent and its dose capable of demonstrating the antitumor effect is extremely close to the dose showing side effects, it is difficult to use the compound as such as an antitumor agent.

The present inventors, with a specific view to increasing the drug therapeutic index, namely the ratio of dose causing the side effect to dose effective for therapy, carried out intensive research. As a result, the present inventors have found that the compounds represented by the formula (I), namely phospholipid compounds whose polar group (substituted ammoniopolymethylene phosphate) has a long methylene chain, show outstanding antitumor activity, but platelet activating actions such as platelet aggregating and blood-pressure lowering actions are surprisingly reduced remarkably and hardly detected in most cases, though these actions have so far been considered to be parallel to the antitumor activity. It has so far been considered that increasing the length of a methylene chain in the polar group (cholinephosphate) of the phospholipid compound induces a decrease in the effect of inhibiting the multiplication of carcinoma cells. (Actually, such an effect is remarkably reduced in the case of a phospholipid compound with a trimethylene chain, as compared with another phospholipid compound with an ethylene chain.) It has been found, however, that an effect of inhibiting the multiplication of carcinoma cells again tends to increase and high activity is finally available by increasing the length of the methylene chain to that having about 8–14 carbon atoms.

Furthermore, it is generally considered that platelet aggregation plays an important role in metastasis of tumor cells. That is, there exists a hypothesis that the adherence of tumor cells to the vessel wall is enhanced through their interaction with platelets and the metastasis of those cells is facilitated. Recently, many researchers have been investigating a possibility of a platelet aggregation inhibitor being effective to prevent the metastasis of carcinoma cells in cancer-bearing animals. The results of such confidence gation are giving many positive answers and in the above hypothesis is increasing. [T. Tsuro et al.: Cancer Chemother Pharmacol. 14, 30 (1985)] According to the hypothesis, the drug possessing platelet aggregation activity, for example, has a possibility of showing an action of facilitating the metastasis of carcinoma cells. On the contrary, the drug possessing platelet aggregation inhibiting activity is expected to show an action of preventing such metastasis. Since the phospholipid compounds of the present invention possess an inhibiting action against platelet aggregation, in addition to the above-mentioned direct cytotoxic action against carcinoma cells, the compounds of the present invention are expected to be effective in preventing the metastasis of carcinoma cells.

Consequently, the pharmacotherapy index for cancer-bearing warm-blooded animals has surprisingly been improved and a remarkable antitumor effect has been found so that the present invention has been completed.

DISCLOSURE OF THE INVENTION

This invention provides a compound of the following formula:

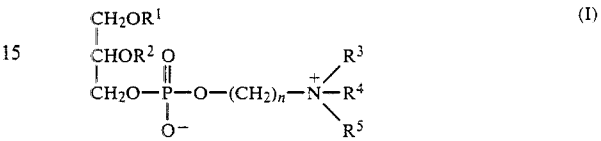

wherein $R^1$ is a higher alkyl, higher acylmethyl or higher alkylcarbamoyl group which may be substituted by cycloalkyl, $R^2$ is a lower alkyl group which may be substituted by carboxy, formyl or lower acyl, or a carbamoyl or thiocarbamoyl group which is substituted by lower alkyl or an acetoacetyl group; $R^3$, $R^4$ and $R^5$ and independently hydrogen or lower alkyl, or

represents a cyclic ammonio group; and n represents an integer of 8 to 14, and a salt thereof.

With reference to the above formula (I), the higher alkyl group represented by $R^1$ includes straight-chain or branched-chain alkyl groups (about $C_{12-20}$), such as n-dodecyl, n-tetradecyl, n-pentadecyl, n-hexadecyl, n-hexadecyl, n-heptadecyl, n-octadecyl, 15-methylhexadecyl, 3,7,11-trimethyldodecyl and 3,7,11,15-tetramethylhexadecyl. As the higher alkylcarbamoyl group represented by $R^1$, there are included various types of alkylcarbamoyl groups in which the alkyl group corresponds to each alkyl group (about $C_{12-20}$) as mentioned above. With respect to the higher acylmethyl group represented by $R^1$, the acyl moiety thereof includes straight or branched-chain alkanoyl groups (about $C_{12-20}$) such as n-tetradecanoyl, n-hexadecanoyl and n-octadecanoyl. The alkyl moieties of the above-mentioned higher alkyl, higher alkylcarbamoyl and higher acylmethyl groups may be substituted by cycloalkyl (about $C_{4-8}$) such as cyclohexyl.

As the lower alkyl group represented by $R^2$, there are included alkyl groups (about $C_{1-5}$), such as methyl, ethyl and propyl. Among these, methyl group is preferable. The lower alkyl group may be substituted by carboxy, formyl or lower acyl. The carboxy-lower alkyl group includes, for example, carboxyalkyl groups (about $C_{2-6}$), such as carboxymethyl, 3-carboxypropyl and 5-carboxypentyl. The formyl-lower alkyl group includes, for example, formylalkyl groups (about $C_{2-6}$), such as formylmethyl, 3-formylpropyl and 5-formylpentyl. Also, as the lower alkyl group substituted by lower acyl (i.e. lower acyl-lower alkyl), there are mentioned alkanoylalkyl groups (about $C_{3-6}$), such as acetylmethyl, acetylpropyl and propionylmethyl. Among these, the acetylmethyl group is preferable. As the carbamoyl group substituted by lower alkyl represented by $R^2$, there are mentioned, N-[lower ($C_{1-5}$)alkyl]carbamoyl groups such as N-methylcarbamoyl and N-ethylcarbamoyl, N,N-di[lower ($C_{1-5}$)alkyl]carbamoyl groups such as N,N-dimethylcarbamoyl and N,N-diethylcarbamoyl. Among these, N-methylcarbamoyl and N,N-dimethylcarbamoyl groups are preferable. The thiocarbamoyl group substituted by lower alkyl represented by $R^2$, includes, for example, N-[lower ($C_{1-5}$)alkyl]thiocarbamoyl groups such as N-methylthiocarbamoyl and N-ethylthiocarbamoyl, and N,N-di[lower ($C_{1-5}$)alkyl]-thiocarbamoyl groups such as N,N-dimethylthiocarbamoyl and N,N-diethylthiocarbamoyl. Among these, the N-methylthiocarbamoyl group is preferable.

$R^3$, $R^4$ and $R^5$ independently represent hydrogen or lower alkyl. The lower alkyl group includes, for examples, $C_{1-5}$ alkyl groups, such as methyl, ethyl, propyl, butyl and pentyl. Among these, the methyl group is preferable.

The cyclic ammonio group represented by

includes pyridinio, oxazolio, thiazolio, pyridazinio, quinolino, isoquinolinio, pyrrolidinio, piperidinio, morpholinio, and piperazinio groups and these groups may further have a substituent such as a lower ($C_{1-4}$) alkyl group (e.g. methyl, ethyl, propyl and butyl), hydroxy group, hydroxyethyl group, aminoethyl group, amino (imino) group, carbamoyl group or ureid group.

Included in the above cyclic ammonio group are groups of the above formula wherein two groups of $R^3$, $R^4$ and $R^5$ form a ring together with the quaternary nitrogen atom and the remaining group is for example lower ($C_{1-4}$)alkyl (e.g. methyl, ethyl, propyl and butyl), thereby forming more particularly such a group as N-methylpyrrolidinio, N-methylmorpholinio, N-methylpiperidinio or N-methylpiperazinio group.

In the compounds (I), there exist two kinds of stereoisomers with R- and S-configurations, and their individual stereoisomers, mixture and racemate are all included in this invention.

The compounds (I) may, in some instances, exist in the form of salts represented by the following formula:

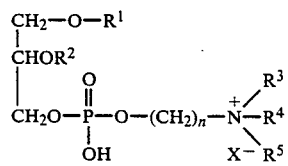

wherein $X^-$ is an anion such as chlorine, bromine or iodine ion.

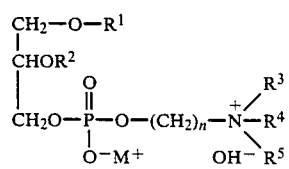

wherein $M^+$ is an alkali metal (e.g. Na and K) ion or an alkaline earth metal (e.g. Ca and Mg). As the salts, pharmaceutically acceptable salts are preferable.

The compound (I) of this invention can be produced, for example, by the following methods:

A compound of the formula:

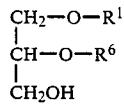

[wherein $R^1$ is the same as defined hereinbefore and $R^6$ represents lower alkyl having about 1–5 carbon atoms (e.g. methyl, ethyl and propyl), protected formyl-lower alkyl having about 2–6 carbon atoms (e.g. dimethoxymethyl, 3,3-diethoxypropyl and 5,5-dimethoxymethyl), protected lower acyl-lower alkyl having about 3–5 carbon atoms (e.g. 2,2-dimethoxypropyl, 4,4-diethoxypentyl and 2,2-dimethoxypentyl), benzyl, benzoyl, N,N-di(lower alkyl)carbamoyl and the like] is prepared [synthesis by the method described in Helv. Chem. Acta. 65, 1059 (1982); ibid, 66, 1210 (1983); Chem. Pharm. Bull (Tokyo), 32, 2700 (1984); the gazette of Japanese Unexamined Patent Publication No. 192825/1983 or any other methods analogous thereto], and a compound of the formula:

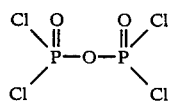

or phosphorus oxychloride is reacted with the above-mentioned compound (VII) in an inert solvent in the presence of a tertiary amine (e.g. pyridine and triethylamine) under the anhydrous condition. Then, the reaction product is reacted with water to give a compound represented by the following formula:

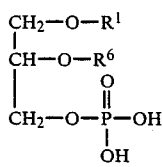

wherein $R^1$ and $R^6$ are the same as defined hereinbefore. This compound (IX) is reacted with a compound represented by the following formula:

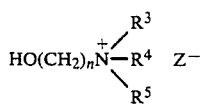

wherein each symbol is the same as defined hereinbefore and $Z^-$ represents an anion such as

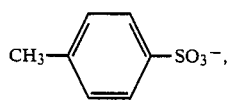

$CH_3COO^-$, $HO^-$ or $Br^-$, in the presence of a condensing agent such as trichloroacetonitrile, 2,4,6-trimethylbenzenesulfonyl chloride, 2,4,6-triisopropylbenzenesulfonyl chloride or 2,4,6-trimethylbenzenesulfonyl imidazolide, to give a compound represented by the following formula:

$$\begin{array}{l} CH_2-O-R^1 \\ CH-O-R^6 \\ \phantom{CH_2-O-}\overset{O}{\underset{|}{\|}} \phantom{xx} R^3 \\ CH_2-O-P-O-(CH_2)_n\overset{+}{N}-R^4 \\ \phantom{CH_2-O-P}\underset{O^-}{|} \phantom{xxxx} \underset{R^5}{|} \end{array} \quad (XI)$$

wherein each symbol is the same as defined hereinbefore, and when $R^6$ is lower alkyl having about 1–5 carbon atoms or N,N-di(lower alkyl)carbamoyl, $R^6$ is equal to $R^2$.

In the above-mentioned reaction, the compound (XI) can also obtained by reacting the compound (VII) with the compound (VIII) or phosphorus oxychloride, and reacting the product with the compound (X) in the presence of the above-mentioned tertiary amine, and then reacting the reaction product with water.

Furthermore, the compound (VII) is reacted with a compound represented by the formula:

$$\begin{array}{c} Cl \phantom{x} O \\ \phantom{x}\diagdown\|\phantom{x} \\ \phantom{xx}P-O(CH_2)_nX \\ \phantom{x}\diagup \\ Cl \end{array} \quad (XII)$$

wherein X represents halogen such as chlorine, bromine or iodine, in an inert solvent in the presence of the aforementioned tertiary amine and further reacted with water, to give a compound represented by the following formula:

$$\begin{array}{l} CH_2-O-R^1 \\ CH-O-R^6 \\ \phantom{CH_2-O-}\overset{O}{\|} \\ CH_2-O-P-O(CH_2)_nX \\ \phantom{CH_2-O-P}| \\ \phantom{CH_2-O-P}O^- \end{array} \quad (XIII)$$

wherein each symbol is the same as defined hereinbefore. The compound (XI) can also be obtained by reacting the compound (XIII) with an amine of the following formula:

$$\begin{array}{l} \phantom{xx}R^3 \\ \phantom{x}\diagup \\ N-R^4 \\ \phantom{x}\diagdown \\ \phantom{xx}R^5 \end{array} \quad (XIV)$$

wherein each symbol is the same as defined hereinbefore.

Referring to the compound (XI) obtained by the above-mentioned methods, when $R^6$ is protected formyllower alkyl or protected lower acyl-lower alkyl, the compound (XI) is subjected to a deprotection reaction by using, for example, an acidic catalyst (e.g. AMBERLITE IR-120(H), acetic acid, para-toluenesulfonic acid, hydrochloric acid and hydrobromic acid) in the presence of water to obtain a compound represented by the formula:

$$\begin{array}{l} CH_2-O-R^1 \\ CH-O-(CH_2)_mCHO \\ \phantom{CH_2-O-}\overset{O}{\|} \phantom{xx} R^3 \\ CH_2O-P-O(CH_2)_n\overset{+}{N}-R^4 \\ \phantom{CH_2-O-P}| \phantom{xxxx} \diagdown \\ \phantom{CH_2-O-P}O^- \phantom{xxxx} R^5 \end{array} \quad (Ic)$$

wherein each symbol is the same as defined hereinbefore and m represents an integer of 1 to 5; or the formula:

$$\begin{array}{l} CH_2-O-R^1 \phantom{xx} O \\ \phantom{CH_2-O-R^1}\| \\ CH-O-(CH_2)_pC(CH_2)_qCH_3 \\ \phantom{CH_2-O-}\overset{O}{\|} \phantom{xx} R^3 \\ CH_2O-P-O(CH_2)_n\overset{+}{N}-R^4 \\ \phantom{CH_2-O-P}| \phantom{xxxx} \diagdown \\ \phantom{CH_2-O-P}O^- \phantom{xxxx} R^5 \end{array} \quad (Id)$$

wherein each symbol is the same as defined hereinbefore, p represents an integer of 1 or more and p+q represents an integer of 1 to 4, each compound falling within the desired formula (I). By oxidizing the compound (Ic), the corresponding carboxy derivative [compound of the formula (I) wherein $R^2$ is carboxy-lower alkyl] can be obtained. The desired object can be achieved by air oxidation, but the reaction may be carried out in the presence of an oxidizing agent.

Referring to the compound (XI), a compound represented by the following formula:

$$\begin{array}{l} CH_2-O-R^1 \\ CH_2O-CH_2C_6H_5 \\ \phantom{CH_2-O-}\overset{O}{\|} \phantom{xx} R^3 \\ CH_2O-P-O(CH_2)_n\overset{+}{N}-R^4 \\ \phantom{CH_2-O-P}| \phantom{xxxx} \diagdown \\ \phantom{CH_2-O-P}O^- \phantom{xxxx} R^5 \end{array} \quad (XIa)$$

wherein each symbol is the same as defined hereinbefore, is subjected to a per se known catalytic reduction reaction; or a compound represented by the following formula:

$$\begin{array}{l} CH_2-O-R^1 \\ CHOCOC_6H_5 \\ \phantom{CH_2-O-}\overset{O}{\|} \phantom{xx} R^3 \\ CH_2O-P-O(CH_2)_n\overset{+}{N}-R^4 \\ \phantom{CH_2-O-P}| \phantom{xxxx} \diagdown \\ \phantom{CH_2-O-P}O^- \phantom{xxxx} R^5 \end{array} \quad (XIb)$$

wherein each symbol is the same as defined hereinbefore, is subjected to a hydrolysis reaction to obtain a compound represented by the following formula:

$$\begin{array}{l} CH_2-O-R^1 \\ CH-OH \\ \phantom{CH_2-O-}\overset{O}{\|} \phantom{xx} R^3 \\ CH_2O-P-O(CH_2)_n\overset{+}{N}-R^4 \\ \phantom{CH_2-O-P}| \phantom{xxxx} \diagdown \\ \phantom{CH_2-O-P}O^- \phantom{xxxx} R^5 \end{array} \quad (XV)$$

wherein each symbol is the same as defined hereinbefore. The above-mentioned hydrolysis reaction can preferably be carried out in the presence of a tetraalkylammonium hydroxide such as tetra-n-butylammonium hydroxide.

The compound (XV) obtained by the above-mentioned methods is reacted with a compound represented by the formula:

$$R^7NCY \qquad (XVI)$$

wherein $R^7$ is lower alkyl and Y represents oxygen or sulfur atom, to give a compound represented by the formula:

$$\begin{array}{l} CH_2-O-R^1 \\ | \quad\quad Y \\ | \quad\quad \| \\ CH-O-C-NHR^7 \\ | \quad\quad O \quad\quad R^3 \\ | \quad\quad \| \quad\quad +/ \\ CH_2O-P-O(CH_2)_nN-R^4 \\ | \quad\quad\quad\quad\quad\quad \backslash \\ O^- \quad\quad\quad\quad\quad\quad R^5 \end{array} \qquad (Ie)$$

wherein each symbol is the same as defined hereinbefore, which falls within the formula (I). The reaction of diketene with the compound (XV) gives a compound represented by the formula:

$$\begin{array}{l} CH_2-O-R^1 \\ | \\ CHOCOCH_2COCH_3 \\ | \quad\quad O \quad\quad R^3 \\ | \quad\quad \| \quad\quad +/ \\ CH_2O-P-O(CH_2)_nN-R^4 \\ | \quad\quad\quad\quad\quad\quad \backslash \\ O^- \quad\quad\quad\quad\quad\quad R^5 \end{array} \qquad (If)$$

wherein each symbol is the same as defined hereinbefore. Both of the above addition reactions can preferably be carried out in the presence of the aforementioned tertiary amine.

The compound (XV) is reacted with phenyl chlorocarbonate to give a compound represented by the formula:

$$\begin{array}{l} CH_2-O-R^1 \\ | \\ CHOCOOC_6H_5 \\ | \quad\quad O \quad\quad R^3 \\ | \quad\quad \| \quad\quad +/ \\ CH_2O-P-O(CH_2)_nN-R^4 \\ | \quad\quad\quad\quad\quad\quad \backslash \\ O^- \quad\quad\quad\quad\quad\quad R^5 \end{array} \qquad (XVII)$$

wherein each symbol is the same as defined hereinbefore. The compound (XVII) obtained is further reacted with a primary or secondary amine (XVIII) represented by the formula:

$$\begin{array}{l} R^8 \\ \quad \backslash \\ \quad\quad NH \\ \quad / \\ R^9 \end{array} \qquad (XVIII)$$

wherein one of $R^8$ and $R^9$ represents lower alkyl and the other represents hydrogen or lower alkyl to give a compound (Ig) represented by the following formula:

$$\begin{array}{l} CH_2-O-R^1 \\ | \quad\quad\quad\quad R^8 \\ | \quad\quad\quad /\\ CH-OCON \\ | \quad\quad O \quad\quad \backslash R^9 \quad R^3 \\ | \quad\quad \| \quad\quad\quad\quad +/ \\ CH_2O-P-O(CH_2)_nN-R^4 \\ | \quad\quad\quad\quad\quad\quad \backslash \\ O^- \quad\quad\quad\quad\quad\quad R^5 \end{array} \qquad (Ig)$$

wherein each symbol is the same as defined hereinbefore, which falls within the formula (I). Furthermore, a dithiocarbamic acid represented by the formula:

$$\begin{array}{l} R^8 \quad S \\ \quad \backslash \quad \| \\ \quad\quad NC-SH \\ \quad / \\ R^9 \end{array} \qquad (XIX)$$

wherein $R^8$ and $R^9$ are the same as defined hereinbefore, is reacted with the compound (XV) in the presence of a carbodiimide such as dimethylcarbodiimide, diisopropylcarbodiimide or dicyclohexylcarbodiimide, to give a compound (Ih) represented by the formula:

$$\begin{array}{l} CH_2OR^1 \\ | \quad\quad S \quad\quad R^8 \\ | \quad\quad \| \quad /\\ CHOC-N \\ | \quad\quad O \quad \backslash R^9 \quad R^3 \\ | \quad\quad \| \quad\quad\quad\quad +/ \\ CH_2O-P-O(CH_2)_nN-R^4 \\ | \quad\quad\quad\quad\quad\quad \backslash \\ O^- \quad\quad\quad\quad\quad\quad R^5 \end{array} \qquad (Ih)$$

wherein each symbol is the same as defined hereinbefore, which falls within the formula (I).

The above methods relate to the typical ones for producing the compound (I), but methods for producing the compound (I) of this invention should not be limited to the these methods.

The compound (I) and a salt thereof can be administered per se or in association with a pharmaceutically acceptable carrier.

The dosage form of preparations for the antitumor agent of the compound (I) includes a variety of pharmaceutical preparations, such as injectable solutions, tablets, capsules, solutions and ointments, and these can be safely administered parenterally or orally.

Preparation of injectable solutions, injectable solutions for infusion, etc. is conducted in accordance with conventional methods using physiological saline or an aqueous solution containing glucose or another adjuvant. Tablets, capsules, etc. can also be prepared in accordance with conventional methods. These dosage forms, for example in the case of injectable solutions, can be used through a suitable route of administration, such as intravenous and subcutaneous administration or direct application to an affected portion, depending upon the purpose of administration.

Effect

The compounds (I) are observed to produce a remarkable diminution or to be practically negligible in respect of side effects due to platelet activating actions, such as platelet aggregation action, blood-pressure lowering action, vessel permeability increasing action and tissue impairing action. On the other hand, however, antitumor action including a cytotoxic effect against a tumor cell is enhanced and the compounds can be administered to tumor-bearing warm-blooded animals as a safe antitumor agent. The method of administration, the route of administration and the amount of administration can be suitably selected depending upon the object for administration and its symptoms. Normally, the amount of the compound (I) to be administered to tumor-bearing warm-blooded animals is in the range of 0.1 to 150 mg/kg (body weight) and preferably in the range of 2 to 50 mg/kg (body weight). With reference to the frequency of administration, the above-mentioned pharmaceutical preparations are applied at a rate of about once to three times a day, or at an interval of 2 to 7 days. They can also be injected intravenously for infusion over a prolonged period of time in order to maintain the concentration of the medicinal substance in the tissue at a required level for a long period of time.

EXAMPLES

This invention will be illustrated in more detail by the following reference examples and examples, but this invention should not be limited to these.

REFERENCE EXAMPLE 1

1,10-Decanediol monotosylate 174.0 g (1.0 mole) of 1,10-decanediol was added to 1,000 ml of dry triethylamine and 95.0 g (0.5 mole) of p-toluenesulfonyl chloride was added thereto over a period of 6 hours with stirring under ice cooling. The reaction mixture was stirred at room temperature for 16 hours and concentrated under reduced pressure, and 1.5 liters of dichloromethane was added to the residue. The resulting mixture was washed with 100 ml each of water, 2N-HCl, water and an aqueous solution saturated with $NaHCO_3$, respectively in order.

The mixture after filtration was concentrated to dryness under reduced pressure. The residue was purified by column chromatography on silica gel (Merck, Art 7734, 1.7 kg; eluent: chloroform-methanol=99:1–98:2) to give 75.6 g of the above-mentioned compound. (yield: 46.0%)

Thin-layer chromatography (developing solvent: chloroform-methanol=9:1) Rf=0.70.

NMR (90 MHz, $CDCl_3$)δ: 1.25 (16H), 1.42–1.63 (2H), 2.45 (3H), 3.62 (2H), 4.01 (2H), 7.31 (2H), 7.78 (2H)

REFERENCE EXAMPLE 2

10-Trimethylammoniodecylalcohol monotosylate 10.6 g (32.2 mmole) of 1,10-decanediol monotosylate was dissolved in 40 ml of 20% trimethylaminetoluene and stirred at room temperature for 3.5 days. The deposited material was collected by filtration and drived to give 10.3 g (yield: 82.4%) of the above-mentioned compound.

NMR (90 MHz, $CDCl_3$-$CD_3OD$)δ: 1.30 (20H), 1.43–1.83 (2H), 2.33 (3H), 3.12 (9H), 3.53 (2H), 7.15 (2H), 7.71 (2H)

REFERENCE EXAMPLE 3

1,14-Tetradecanediol

According to the method of R. F. Nystrom et al. [J. Am. Chem. Soc., 69, 2548 (1947)], 18.5 g (yield: 96.7%) of the above-mentioned compound was obtained from 23.0 g (89.0 mmole) of 1,14tetradecane dicarboxylic acid.

NMR (90 MHz, $CDCl_3$-$CD_3OD$)δ: 1.27 (20H), 1.54 (4H), 3.57 (4H).

IR (KBr) $cm^{-1}$: 3420, 3350, 2920, 2845, 1455, 1355, 1050, 1015, 970, 725

REFERENCE EXAMPLE 4

1,14-Tetradecanediol monotosylate

By following the procedure of Reference Example 1, 18.0 g (84.0 mmole) of 1,14-tetradecanediol was treated to obtain 6.4 g (yield: 39.6%) of the above-mentioned compound.

NMR (90 MHz, $CDCl_3$-$CD_3OD$)δ: 1.34 (20H), 1.67–2.05 (4H), 2.35 (3H), 3.50 (2H), 4.64 (2H), 7.17 (2H), 7.71 (2H), 8.07 (2H), 8.48 (1H), 9.05 (2H)

REFERENCE EXAMPLE 5

14-Trimethylammoniotetradecylalcohol monotosylate

By following the procedure of Reference Example 2, 2.50 g (6.5 mmole) of 1,14-tetradecanediol monotosylate was treated to obtain 1.97 g (yield: 68.4%) of the above-mentioned compound.

NMR (90 MHz, $CDCl_3$-$CD_3OD$)δ: 1.26 (24H), 1.60 (2H), 2.34 (3H), 3.13 (9H), 3.55 (2H), 7.15 (2H), 7.71 (2H)

REFERENCE EXAMPLE 6

1,8-Octanediol monotosylate

By following the procedure of Reference Example 1, 14.4 g (98.0 mmole) of 1,8-octanediol was treated to obtain 7.0 g (yield: 24.7%) of the above-mentioned compound.

NMR (90 MHz, $CDCl_3$)δ: 1.28 (8H), 1.67 (4H), 2.45 (3H), 3.50 (2H), 4.02 (2H), 7.33 (2H), 7.80 (2H)

REFERENCE EXAMPLE 7

8-Trimethylammoniooctylalcohol monotosylate

By following the procedure of Reference Example 2, 3.00 g (10.0 mmole) of 1,8-octanediol monotosylate was treated to obtain 3.24 g (yield: 90.3%) of the above-mentioned compound.

NMR (90 MHz, $CDCl_3$-$CD_3OD$)δ: 1.33 (8H), 1.75 (4H), 2.35 (3H), 3.14 (9H), 3.53 (4H), 7.27 (2H), 7.73 (2H)

REFERENCE EXAMPLE 8

8-Pyridiniooctylalcohol monotosylate 2.50 g (8.32 mmole) of 1,8-octanediol monotosylate was dissolved in 8 ml of dry pyridine and the mixture was stirred at 60° C. for 24 hours. The deposited material was collected by filtration and dried to obtain 3.10 g (yield: 98.2%) of the above-mentioned compound.

NMR (90 MHz, $CDCl_3$-$CD_3OD$)δ: 1.34 (8H), 1.67–2.05 (4H), 2.35 (3H), 3.50 (2H), 4.64 (2H), 7.17 (2H), 7.71 (2H), 8.07 (2H), 8.48 (1H), 9.05 (2H)

REFERENCE EXAMPLE 9

12-Cyclohexyldodecyl bromide

To 98 g (0.30 mole) of 1,12-dibromodecane in 300 ml of anhydrous tetrahydrofuran (THF), cyclohexylmagnesium bromide (0.30 mole) in 300 ml of THF was added dropwise at 10°–15° C. over a period of 1.5 hours in the presence of 0.5 mole percent of dilithium tetrachlorocuprate ($Li_2CuCl_4$), and the reaction mixture was stirred at room temperature overnight. To the mixture was added 16 ml of 2N sulfuric acid to adjust pH to about 2, and about 500 ml of ethyl acetate was further added thereto. The insoluble material was filtered off, and the filtrate was washed with water, saturated sodium bicarbonate solutuion and water, in order and then dried over anhydrous magnesium sulfate. The organic layer was concentrated under reduced pressure and the obtained oil was subjected to distillation under reduced pressure. The distillate having a boiling point of 166–167° C. (0.3 mmHg) was collected to obtain 40 g (yield: 40%) of the above-mentioned compound.

IR (Neat)cm$^{-1}$: 2920, 2850, 1460, 1440

NMR (90 MHz, CDCl$_3$) δ: 1.26 (26H), 1.45–1.93 (7H), 3.45 (2H)

REFERENCE EXAMPLE 10

1-(12-Cyclohexyldodecyloxy)-2,3-propanediol

A mixture of 40.8 g (0.123 mole) of 12-cyclohexyldodecyl bromide, 22.7 g (0.172 mole) of 1,2-isopropylideneglycerol, 1.0 g of cetyltrimethylammonium chloride and 27.6 g (0.344 mole) of 50% aqueous sodium hydroxide solution was stirred at 80° C. for 10 hours. To the reaction mixture was added 200 ml of hexane and the resulting mixture was washed with water, dried (MgSO$_4$) and concentrated under reduced pressure. To the residue were added 200 ml of methanol and 4 ml of 6N hydrochloric acid, and the mixture was heated unde reflux for 10 hours. The mixture was cooled and the colorless crystals precipitated were collected by filtration, washed with hexane and dried to give 10.1 g of the above-mentioned compound. The mother liquid was further cooled to obtain 20.8 g of the second crystals. Total yield: 30.9 g (yield: 74%)

IR (KBr)cm$^{-1}$: 3375, 2920, 2850, 1460, 1325, 1120, 1055, 935

NMR (90 MHz, CDCl$_3$) δ: 1.25 (26H), 1.47–1.74 (7H), 2.50 (1H), 2.85 (1H), 3.37–3.80 (6H), 3.85 (1H)

REFERENCE EXAMPLE 11

3-(12-Cyclohexyldodecyloxy)-2-methoxypropanol

A mixture of 23.5 g (68.6 mmole) of 1-(12-cyclohexyldodecyloxy)-2,3-propanediol, 28.7 g (103 mmole) of trityl chloride, 13.7 g (137 mmole) of triethylamine and 200 ml of dichloromethane was stirred at room temperature for 2 days. To the reaction mixture was added 10 ml of methanol and the resulting mixture was further stirred for 3 hours. The mixture was washed with water and dried (MgSO$_4$) and the solvent was distilled off to give 52 g (quantitative) of crude 1-(12-cyclohexyldodecyloxy)-3-trityloxy-2-propanol. In 100 ml of tetrahydrofuran (THF) was dissolved 17 g (23 mmole) of this product, and 1.84 g (46 mmole) of 60% sodium hydride was added thereto. The mixture was stirred at room temperature for 1 hour and 4 ml of methyl iodide was added to the mixture. The reaction mixture was stirred at room temperature overnight and then 5 ml of methanol was added thereto. The solvent was distilled off under reduced pressure, and the residue was dissolved in 200 ml of hexane and washed with water and 1N hydrochloric acid, in order. After hexane was distilled off, 30 ml of 1N hydrochloric acid and 60 ml of dioxane were added to the residue, and the mixture was stirred at 80° C. for 10 hours. The mixture was neutralized with sodium bicarbonate and then 60 ml of ethyl acetate was added to the mixture. The resulting mixture was washed with water and dried (MgSO$_4$), and the solvent was distilled off. The residue was subjected to column chromatography on silica gel (200 g) and eluted with dichloromethane-ethyl acetate (5:1) to give 6.6 g (yield: 81%) of the above-mentioned compound as colorless solid.

IR (KRr)cm$^{-1}$: 3450, 2925, 2850, 1465, 1445, 1120

NMR (90 MHz, CDCl$_3$) δ: 1.24 (26H), 1.47–1.77 (7H), 2.15 (1H), 3.36–3.80 (7H), 3.45 (3H)

REFERENCE EXAMPLE 12

2-Benzyloxy-3-(12-cyclohexyldodecyloxy)propanol

A mixture of 35 g (4.6 mmole) of 1-(12-cyclohexyldodecyloxy)-3-trityloxy-2-propanol prepared in Reference Example 11, 8.7 g (69 mmole) of benzyl chloride, 0.5 g of cetyltrimethylammonium chloride, 7.4 g (92 mmole) of 50% aqueous sodium hydroxide solution and 50 ml of THF was stirred at 60° C. overnight. To the reaction mixture were further added 7.4 g (92 mmole) of 50% aqueous sodium hydroxide solution and 8.7 g (69 mmole) of benzyl chloride, and the resulting mixture was stirred overnight. THF was distilled off from the mixture, and 100 ml of hexane was added to the residue. The mixture was washed with water and then hexane was distilled off. To the residue were added 120 ml of dioxane and 60 ml of 1N hydrochloric acid, and the mixture was stirred at 80° C. for 5 hours. After the mixture was cooled and neutralized with sodium bicarbonate, 100 ml of ethyl acetate was added to the mixture. The organic layer was washed with water and dried (MgSO$_4$), and then the solvent was distilled off. The residue was allowed to stand at room temperature overnight. A small amount of hexane was added to the residue and the deposited tritylalcohol was filtered off. The filtrate was subjected to column chromatography on silica gel (500 g) and eluted with hexane-ethyl acetate (9:1) to give 9.0 g (yield: 45%) of the above-mentioned compound as a colorless oil.

IR (Neat)cm$^{-1}$: 3420, 2920, 2850, 1465, 1450, 1115, 1060, 735, 695

NMR (90 MHz, CDCl$_3$) δ: 1.26 (26H), 1.50–1.78 (7H), 3.37–3.72 (8H), 4.68 (2H), 7.37 (5H)

EXAMPLE 1

2-(Benzoyloxy)-3-(octadecyloxy)propyl 10-trimethylammoniodecyl phosphate 2.24 g (5.0 mmole) of 2-benzoyloxy-3-octadecyloxypropanol was dissolved in 20 ml of ethanol-free chloroform and 2.63 g (26.0 mmole) of dry triethylamine was added thereto under ice-cooling. Then, 0.81 g (5.3 mmole) of phosphorus oxychloride in 40 ml of ethanol-free chloroform was further added, and the resulting mixture was stirred under ice-cooling for 30 minutes and at room temperature for 1 hour. This reaction mixture was again cooled on ice, and 2.80 g (7.5 mmole) of 10-trimethylammoniodecylalcohol monotosylate in 80 ml of dry pyridine was added thereto. The reaction mixture was stirred under ice-cooling for 30 minutes and at room temperature for 18 hours. To the reaction mixture was added an aqueous solution containing 3.5 g sodium hydrogencarbonate and the resulting mixture was concentrated to dryness under reduced pressure. The residue was purified by column chromatography on Amberlite resin (IR-120: IRA-410=1:2; eluent: 95% THF) and then further by column chromatography on silica gel (Merck, Art 7734; eluent: chloroform-methanol-water=65:25:4) to give 1.57 g (yield: 43.4%) of the desired product.

Thin-layer chromatography (developing solvent: chloroform-methanol:water=65:25:4) Rf=0.55

NMR (90 MHz, CDCl₃) δ: 0.88 (3H), 1.27 (38H), 1.53 (2H), 3.11 (9H), 3.40–4.34 (12H), 5.39 (1H), 7.55 (3H), 8.07 (2H)

EXAMPLE 2

2-(Hydroxy)-3-(octadecyloxy)propyl 10-trimethylammoniodecyl phosphate 1.57 g (2.1 mmole) of the compound of Example 1 was dissolved in 10 ml of methanol and an aqueous solution containing 12.4 g (4.8 mmole) of 10% tetra-n-butylammonium hydroxide was added thereto. After stirring at room temperature for 28 hours, the reaction mixture was concentrated to dryness under reduced pressure, and the residue was crystallized from actone to obtain 1.18 g (yield: 87.4%) of the desired product.

Thin-layer chromatography (developing solvent: chloroform-methanol:water=65:25:4) Rf=0.25

NMR (90 MHz, CDCl₃-CD₃OD) δ: 0.89 (3H), 1.26 (30H), 1.35 (14H), 1.65 (4H), 3.11 (9H), 3.23–3.48 (6H), 3.87 (4H), 4.11 (3H)

EXAMPLE 3

2-(Acetoacetyloxy)-3-(octadecyloxy)propyl 10-trimethylammoniodecyl phosphate

In a mixture of 20 ml of dry dichloromethane and 20 ml of dry pyridine was dissolved 994 mg (0.6 mmole) of the compound of Example 2 and 2 ml of diketene was added thereto. The reaction mixture was stirred at room temperature for 17 hours, and then concentrated to dryness under reduced pressure. The residue was purified by silica gel column chromatography (Merck & Co., Art. 7734; eluent: chloroform-methanol-water=65:25:4) to give 843 mg (yield: 74.7%) of the desired product.

Thin-layer chromatography (developing solvent: chloroform-methanol:water=65:25:4) Rf=0.29

NMR (90 MHz, CDCl₃-CD₃OD) δ: 0.88 (3H), 1.26 (30H), 1.36 (8H), 1.63 (2H), 2.27 (3H), 3.11 (9H), 3.23–3.50 (4H), 3.62 (2H), 3.80–4.02 (4H), 5.20 (1H)

IR (KBr)cm⁻¹: 3420, 2930, 2860, 1745, 1720, 1635, 1465, 1230, 1075, 840

EXAMPLE 4

2-(Benzyloxy)-3-(octadecyloxy)propyl 10-trimethylammoniodecyl phosphate 2.34 g (5.4 mmole) of 2-benzyloxy-3-octadecyloxy-propanol was dissolved in 20 ml of ethanol-free chloroform and 2.83 g (28.0 mmole) of dry triethylamine was added thereto under ice-cooling. Then, 0.87 g (5.7 mmole) of phosphorus oxychloride in 40 ml of ethanol-free chloroform was further added. The reaction mixture was stirred under ice-cooling for 30 minutes and at room temperature for 1 hour. This reaction mixture was again cooled on an ice bath and 3.00 g (8.07 mmole) of 10-trimethylammoniodecylalcohol monotosylate in 80 ml of dry pyridine was added to the mixture. The resulting mixture was stirred under ice-cooling for 30 minutes and at room temperature for 16 hours. An aqueous solution containing 3.8 g of sodium hydrogencarbonate was added to the reaction mixture and the reaction mixture was concentrated to dryness under reduced pressure. The residue was purified by Amberlite resin column chromatography (IR-120: IRA-410=1:2; eluent: 95% THF) and by silica gel column chromatography (Merck & Co., Art. 7734, eluent: chloroform-methanol:water=65:25:4) to give 1.32 g (yield: 34.3%) of the desired product.

EXAMPLE 5

2-(Hydroxy)-3-(octadecyloxy)propyl 10-trimethylammoniodecyl phosphate 1.31 g (1.8 mmole) of the compound of Example 4 was dissolved in a mixture of 100 ml of ethanol and 50 ml of 70% acetic acid. Then, 0.6 g of 10% Pd-C was added thereto and catalytic reduction was carried out at room temperature. 19 hours later, the reaction mixture was filtered and the filtrate was concentrated to dryness under reduced pressure. The residue was solidified by acetone to give 994 mg (yield: 87.2%) of the desired product.

Thin-layer chromatography (developing solvent: chloroform-methanol:water=65:25:4) Rf=0.25

NMR (90 MHz, CDCl₃-CD₃OD) δ: 0.89 (3H), 1.26 (30H), 1.35 (14H), 1.60 (4H), 3.13 (9H), 3.20–3.52 (6H), 3.78–3.93 (4H), 4.12 (1H)

EXAMPLE 6

2-Methoxy-3-(2-oxoeicocyloxy)propyl 10-trimethylammoniodecyl phosphate

By following the procedure of Example 1, 1.6 g of 2-methoxy-3-(2-oxoeicocyloxy)propanol as a starting material was treated to give 702 mg (yield: 25.9%) of the desired product.

IR (KBr)cm⁻¹: 3400 (broad), 2920, 2850, 1720, 1460, 1220, 1060

NMR (CDCl₃) δ: 0.86 (3H, t), 1.2–1.9 (16H, m), 1.24 (32H, m), 2.73 (2H, t), 3.30 (9H, s), 3.43 (3H, s), 3.2–3.9 (9H, m), 4.09 (2H, s)

TLC: Rf=0.22 (CHCl₃:MeOH:H₂O=65:25:4)

EXAMPLE 7

2-(Benzyloxy)-3-(octadecyloxy)propyl 10-trimethylammoniodecyl phosphate 5.3 g of 10-bromodecyl dichlorophosphate was dissolved in 30 ml of toluene and 3.5 ml of triethylamine was dropwise added thereto with stirring under ice-cooling. To the reaction mixture, 4.35 g of 2-(benzyloxy)-3-(octadecyloxy)propanol in toluene (20 ml) was dropwise added and the resulting mixture was stirred at room temperature for 3 hours. To the mixture was added 20 ml of 2N HCl, and the mixture was stirred at 50° C. for 1 hour. The mixture was extracted with ether and the ether layer was washed with water, dried (MgSO₄) and concentrated under reduced pressure. The obtained oily material was dissolved in 20% (W/W) trimethylamine in toluene (50 ml) and the mixture was stirred at room temperature for 3 days. The reaction mixture was concentrated under reduced pressure, and the residue was purified by silica gel column chromatography (eluent: chloroform:methanol:-water=65:25:4) to give 3.37 g (yield: 47.3%) of the desired product.

IR (KBr)cm⁻¹: 3400 (broad), 2920, 2850, 1620, 1465, 1210, 1090, 1050

NMR (CDCl₃+CD₃OD) δ: 0.87 (3H, t), 1.29 (32H, m), 1.1–2.0 (16H, m), 3.22 (9H, m), 3.3–4.0 (11H, m), 4.68 (2H, s), 7.32 (5H, s)

EXAMPLE 8

2-Methylcarbamoyloxy-3-octadecyloxypropyl 10-trimethylammoniodecyl phosphate 350 mg of the compound obtained in Example 2 and 2 ml of methyl isocyanate were dissolved in 5 ml pyridine and the mixture was stirred at 50° C. for 4 hours. Then, the mixture was concentrated under reduced presssure, and the residue was purified by silica gel column chromatography (eluent: chloroform:methanol:water=65:25:4) to obtain 270 mg of the desired product.

IR (KBr)cm$^{-1}$: 3400 (broad), 2920, 2850, 1710, 1460, 1230, 1065

NMR (CDCl$_3$) δ: 0.86 (3H, t), 1.28 (32H, s), 1.2–2.1 (16H, m), 2.69 (3H, d, J=5 Hz), 3.15 (9H, s), 3.1–4.2 (10H, m), 4.87 (1H, m), 6.29 (1H, broad, s)

Thin-layer chromatography (developing solvent: chloroform:methanol:water=65:25:4) Rf=0.16

EXAMPLE 9

2-Methylthiocarbamoyloxy-3-octadecyloxypropyl 10-trimethylammoniodecyl phosphate The alcohol obtained in Example 2 was reacted with methyl isothiocyanate according to Example 8 to give the desired product.

IR (KBr)cm$^{-1}$: 3400 (broad), 2920, 2850, 1460, 1230, 1065

NMR (CDCl$_3$) δ: 0.86 (3H, t), 1.1–2.1 (16H, m), 1.31 (32H, s), 3.00 (3H, d), 3.1–4.1 (11H, m), 3.28 (9H, s), 5.6 (1H, broad, s)

TLC: RF=0.17 (CHCl$_3$:CH$_3$OH:H$_2$O=65:25:4)

EXAMPLE 10

2-Methoxy-3-octadecyloxypropyl 10-trimethylammoniodecyl phosphate

In accordance with Example 7, 2.15 g of 2-methoxy-3-octadecyloxypropanol, 3.17 g of 10-bromodecyl dichlorophosphate and trimethylamine were reacted and the purification was carried out to give 2.47 g (yield: 64.8%) of the desired product.

IR (KBr)cm$^{-1}$: 3400, 2920, 2855, 1640, 1465, 1230, 1070

NMR (90 MHz, CDCl$_3$) δ: 0.85 (3H, t), 1.1–1.9 (48H, m) 3.31 (9H, s), 3.40 (3H, s), 3.2–4.0 (11H, m)

TLC: Rf=0.19 (CHCl$_3$-MeOH-H$_2$O=65:25:4)

EXAMPLE 11

3-Octadecylcarbamoyloxy-2-methoxypropyl 10-trimethylammoniodecyl phosphate

In accordance with Example 1, 0.67 g of 3-octadecylcarbamoyloxy-2-methoxypropanol was used for reaction and purification to give 0.59 g of the desired product.

IR (KBr)cm$^{-1}$: 3400, 2920, 2850, 1700, 1635, 1460, 1230, 1070

NMR (90 MHz, CDCl$_3$+CD$_3$OD) δ: 0.87 (3H, t), 1.25 (32H, m), 1.35 (16H, m), 2.95–3.2 (2H, m), 3.11 (9H, s), 3.43 (3H, s), 3.3–4.05 (7H, m), 4.11 (2H, m)

TLC: Rf=0.2 (CHCl$_3$-MeOH-H$_2$0=65:25:4)

EXAMPLE 12

1-Benzyl-2-(2,3-epoxypropyl)-3-octadecylglycerol 34.7 g (80 mmole) of 1-benzyl-3-octadecylglycerol was dissolved in 300 ml of hexane and 3.7 g (92 mmole) of 60% oily sodium hydride was added thereto. The mixture was stirred at room temperature for 30 minutes, and then 33 g (240 mmole) of epibromohydrin was added dropwise thereto over a period of 5 minutes. The reaction mixture was stirred at room temperature for 15 hours, and then poured into water. The upper layer was separated and dried over anhydrous magnesium sulfate. The low-boiling material was distilled off under reduced pressure and the residue was purified by silica gel column chromatography to obtain 31.9 g (yield: 81%) of the above-identified compound. The eluent consisted of hexane, acetone and ethyl acetate in a ratio of 30:1:1–10:1:1.

IR (neat)cm$^{-1}$: 1110, 1100

NMR (60 MHz, CDCl$_3$) δ: 0.87 (3H), 1.23 (32H), 2.53–2.83 (2H), 3.00–3.23 (1H), 3.30–3.83 (9H), 4.53 (2H), 7.27 (5H)

EXAMPLE 13

1-Benzyl-2-(2-hydroxypropyl)-3-octadecylglycerol 16.6 g of 1-benzyl-2-(2,3-epoxypropyl)-3-octadecylglycerol in 100 ml of ether was dropwise added to 760 mg of lithium alminum hydride in 50 ml of ether with stirring.

After completion of the addition, the mixture was stirred at room temperature for 2 hours and 360 mg of lithium aluminum hydride was added thereto. Then, the mixture was further stirred at room temperature for 1 hour. 10 ml of acetone was dropwise added thereto and 15 ml of concentrated hydrochloric acid dissolved in 50 ml of water was further added dropwise. Then, the reaction mixture was stirred at room temperature for 1 hour, and the upper layer was separated, washed with an aqueous solution of sodium bicarbonate and dried over anhydrous magnesium sulfate. Finally, ether was distilled off under reduced pressure to give 16.6 g (yield: 100%) of the above-identified compound.

IR (neat)cm$^{-1}$: 3430, 1095

NMR (60 MHz, CDCl$_3$) δ: 0.90 (3H), 1.10 (3H), 1.27 (32H), 3.30–3.93 (10H), 4.57 (2H), 7.27 (5H)

EXAMPLE 14

1-Benzyl-3-octadecyl-2-(2-oxopropyl)glycerol 16.6 g of 1-benzyl-2-(2-hydroxypropyl)-3-octadecylglycerol was dissolved in 500 ml of acetone. To the reaction mixture, a mixture obtained by dissolving chrominum oxide (VI) in a solution of 4.4 ml of concentrated sulfuric acid diluted with 7.6 ml of water and further by adding water thereto to a total volume of 19 ml, was added dropwise over a period of about 10 minutes with stirring at room temperature. The reaction mixture was stirred for 10 minutes under the same conditions as the above, and further stirred for 30 minutes after addition of 10 ml of isopropanol. Then, 15 g of sodium bicarbonate was added thereto and the mixture was vigorously stirred for 30 minutes. The insoluble material was filtered off and 100 ml of water was added. Acetone was distilled off under reduced pressure, and 100 ml of water and 200 ml ether were added to the residue. The upper layer was dried over anhydrous magnesium sulfate, and ether was distilled off under reduced pressure. The residue was purified by silica gel column chromatography to give 14 g (yield: 84%) of the above-identified compound. The eluent consisted of hexane, ethyl acetate and acetone in a ratio of 24:1:1.

IR (neat)cm$^{-1}$: 1720, 1135, 1115, 1105

NMR (60 MHz, CDCl$_3$) δ: 0.87 (3H), 1.23 (32H), 2.13 (3H), 3.27–3.80 (7H), 4.20 (2H), 4.50 (2H), 7.23 (5H)

EXAMPLE 15

3-Octadecyl-2-(2-oxopropyl)glycerol

Hydrogenolysis of 6.5 g (13.3 mmole) of 1-benzyl-3-octadecyl-2-(2-oxopropyl)glycerol was carried out in a mixture of 100 ml of acetic acid, 20 ml of water and 20 ml of ethanol using 2.5 g of 10% palladium carbon (50% wet) at ambient temperature under atmospheric pressure. 100 ml of acetone was added and the mixture was heated up to 50° C. Then, the catalyst was filtered off and 100 ml of 2-methylpropanol was added. Furthermore, the mixture was concentrated to dryness under reduced pressure. 100 ml of toluene was added to the residue and the mixture was again concentrated to dryness. 70 ml of hexane was added to the residue, and the crystals precipitated were collected by filtration to give 3.9 g (yield: 74%) of the above-identified compound.

This compound exists mainly in the form of hemikethal.

IR (Nujol)cm$^{-1}$: 3420, 1135, 875

NMR (60 MHz, CDCl$_3$-CD$_3$OD) δ: 0.90 (3H), 1.27 (35H), 3.40–4.00 (9H)

EXAMPLE 16

1-Benzyl-2-(2,2-dimethoxy)propyl-3-octadecylglycerol 11.8 g (24 mmole) of 1-(benzyl)-3-octadecyl-2-(2-oxo)propylglycerol was dissolved in 120 ml of 2,2-dimethoxypropane and 4 g of D-camphor-10-sulfonic acid was added thereto. The mixture was stirred at room temperature for 17 hours, and the reaction mixture was poured into a mixture of sodium bicarbonate and 100 ml of water with vigorous stirring. 150 ml of ether was added thereto and the ether layer was separated, washed with water and dried over anhydrous magnesium sulfate. Then, ether was distilled off and the residue was purified by silica gel column chromatography to give 11.8 g (yield: 92%) of the above-identified compound.

IR (neat)cm$^{-1}$: 1250, 1115, 1065, 850

NMR (60 MHz, CDCl$_3$): 0.87 (3H), 1.23 (32H), 1.33 (3H), 3.23 (6H), 3.27–3.73 (9H), 4.53 (2H), 7.33 (5H)

EXAMPLE 17

2-(2,2-Dimethoxy)propyl-3-octadecylglycerol 11.8 g (22 mmole) of 1-benzyl-2-(2,2-dimethoxy)propyl-3-octadecylglycerol was dissolved in 200 ml of ethanol and 3 g of 10% palladium carbon was added thereto. Hydrogenolysis was carried out at room temperature under atmospheric pressure. The catalyst was filtered off and the solvent was distilled off under reduced pressure to give 9.8 g (yield: 100%) of the above-identified compound.

IR (neat)cm$^{-1}$: 3440, 1250, 1185, 1170, 1120, 1050, 850

NMR (60 MHz, CDCl$_3$) δ: 0.87 (3H), 1.23 (32H), 1.37 (3H), 2.67 (1H), 3.23 (6H), 3.30–3.83 (9H)

EXAMPLE 18

3-(Octadecyloxy)-2-(2-oxopropyloxy)propyl 10-trimethylammoniodecyl phosphate 1.72 g (3.9 mmole) of 2-(2,2-dimethoxy)propyl-3-octadecylglycerol and 2.3 g (23 mmole) of triethylamine were dissolved in 10 ml of dichloromethane. While the mixture was stirred on an ice bath, 627 mg (4.1 mmole) of phosphorus oxychloride was added thereto. The ice bath was removed, and the mixture was stirred for 2 hours.

2 g (5.2 mmole) of 10-hydroxydecyltrimethylammonium para-toluenesulfonate in 10 ml of pyridine was added to the mixture with stirring on an ice bath. The mixture was further stirred for 2 hours after removal of the ice bath. Dichloromethane was distilled off, and the residue was stirred at 40°–45° C. for 0.5 hour. 10 ml of pyridine and 2 ml of water were added and the resulting reaction mixture was stirred at the same temperature for 0.5 hour and then concentrated to dryness under reduced pressure.

The residue was dissolved in 95% tetrahydrofuran and passed through two columns, one containing 20 ml volume of Amberlite IR-120 (H) and the other containing 20 ml volume of IRA-401 (OH) for desalting and then concentrated to dryness under reduced pressure.

The residue was dissolved in 50 ml of 90% tetrahydrofuran and 9 ml of Amberlite IR-120 (H) was added thereto. The mixture was stirred at 40° C. for 4 hours, and the ion-exchange resin was filtered off and then the resulting mixture was concentrated to dryness under reduced pressure.

The residue was purified by silica gel column chromatography to give 620 mg (yield: 24%) of the above-identified compound.

IR (CHCl$_3$)cm$^{-1}$: 1730, 1230, 1200, 1095, 1070

NMR (60 MHz, CDCl$_3$-CD$_3$OD) δ: 0.90 (3H), 1.27 (32H), 1.37 (16H), 2.17 (3H), 3.17 (9H), 3.30–4.20 (11H), 4.53 (2H)

EXAMPLE 19

2-Dimethylcarbamoyloxy-3-octadecyloxypropyl 10-trimethylammoniodecyl phosphate In accordance with Example 7, 2.49 g of 2-dimethylcarbamoyloxy-3-octadecyloxypropanol, 3.17 g of 10-bromodecyl chlorophosphate and trimethylamine were used for reaction and purification to give 2.55 g (yield: 61.3%) of the desired product.

IR (KBr)cm$^{-1}$: 3450, 2920, 2855, 1700, 1495, 1460, 1400, 1200, 1070

NMR (90 MHz, CDCl$_3$) δ: 0.87 (3H, t), 1.1–1.9 (48H, m), 2.87 (6H, s), 3.33 (9H, s), 3.1–4.0 (11H, m)

TLC: Rf=0.18 (CHCl$_3$-MeOH-H$_2$O=65:25:4)

EXAMPLE 20

1-Benzyl-2-(2,2-dimethoxy)ethyl-3-octadecylglycerol

A mixture of 13.1 g (30 mmole) of 2-benzyl-3-octadecylglycerol, 8.5 g (50 mmole) of bromoacetaldehydedimethylacetal, 192 mg of cetyltrimethylammonium chloride and 12 g of 50% sodium hydroxide was stirred at 85° C. for 20 hours. After the mixture was cooled, hexane was added thereto and the material soluble in hexane was extracted. Hexane was distilled off under reduced pressure and the residue was purified by silica gel column chromatography to give 10.1 g (yield: 64%) of the above-identified compound. A mixture of hexane-ethyl acetate-acetone (24:1:1) was used as the eluent.

IR (neat)cm$^{-1}$: 1205, 1115

NMR (60 MHz, CDCl$_3$) δ: 0.90 (3H), 1.27 (32H), 3.33 (6H), 3.40–3.90 (9H), 4.50 (1H), 4.53 (2H), 7.27 (5H)

EXAMPLE 21

2-(2,2-Dimethoxy)ethyl-3-octadecylglycerol 10 g (19 mmole) of 1-benzyl-2-(2,2-dimethoxy)ethyl-3-octadecylglycerol was dissolved in 150 ml of ethanol and 2.5 g of 10% palladium carbon was added thereto. Hydrogenolysis was carried out in hydrogen atmosphere at room temperature under atmospheric pressure. The catalyst was filtered off and ethanol was distilled off under reduced pressure to give 7.9 g (yield: 95%) of the above-identified compound.

IR (neat)cm$^{-1}$: 3430, 1110

NMR (60 MHz, CDCl$_3$) δ: 0.90 (3H), 1.27 (32H), 2.57 (1H), 3.30–3.70 (15H), 4.50 (1H)

EXAMPLE 22

2-(2,2-Dimethoxy)ethyloxy-3-octadecyloxypropyl 10-trimethylammoniodecyl phosphate 1.7 g (4 mmole) of 2-(2,2-dimethoxy)ethyl-3-octadecylglycerol and 2.4 g (24 mmole) of triethylamine were dissolved in 12 ml of dichloromethane and 649 mg (4.2 mmole) of phosphorus oxychloride was added thereto with stirring on an ice bath. Immediately, the ice bath was removed and the mixture was stirred for 1 hour. While the mixture was again stirred on an ice bath, 2.0 g (5.2 mmole) of 10-hydroxydecyltrimethylammonium p-toluenesulfonate dissolved in 10 ml of pyridine was added. The ice bath was immediately removed and the mixture was stirred at room temperature for 16 hours.

Dichloromethane was distilled off under reduced pressure and 2 ml of water was added. The mixture was stirred at 45° C.–50° C. for 0.5 hour and concentrated to dryness under reduced pressure. 10 ml of 95% cold tetrahydrofuran was added to the residue and the insoluble substances were filtered off. The filtrate was passed through two columns, one containing 20 ml volume of Amberlite IR-120 (H) and the other 20 ml volume of Amberlite IRA-401 (OH) for desalting, and then eluted with 95% tetrahydrofuran.

The eluate was concentrated to dryness under reduced pressure and the residue was purified by silica gel column chromatography to give 1.7 g (yield: 60%) of the above-identified compound.

IR (CHCl$_3$)cm$^{-1}$: 1230, 1210, 1090, 1065, 970

NMR (60 MHz, CDCl$_3$-CD$_3$OD) δ: 0.87 (3H), 1.23 (32H), 1.33 (16H), 3.10 (9H), 3.37 (6H), 3.40–4.00 (13H), 4.47 (1H)

EXAMPLE 23

2-(Formylmethyloxy)-3-(octadecyloxy)propyl 10-trimethylammoniodecyl phosphate 0.82 g of 2-(2,2-dimethoxy)ethyl-3-(octadecyloxy)propyl 10-trimethylammoniodecyl phosphate was dissolved in 40 ml of 80% tetrahydrofuran and 4 ml of Amberlite IR-120 (H) was added thereto. The mixture was stirred at 45° C. for 42 hours and the resin filtered off. The filtrate was concentrated to dryness under reduced pressure, and the residue was purified by silica gel column chromatography to give 298 mg (yield: 39%) of the above-identified compound. A mixture of chloroform-methanol-water (65:25:4) was used as the eluent.

This product exists as the hydrate.

IR (CHCl$_3$)cm$^{-1}$: 1220, 1185, 1100, 1070, 965

NMR (60 MHz, CDCl$_3$-CD$_3$OD) δ: 0.90 (3H), 1.27 (32H), 1.37 (16H), 3.13 (9H), 3.30–4.10 (13H), 4.60–4.80 (1H)

EXAMPLE 24

2-(Benzyloxy)-3-(octadecyloxy)propyl 14-trimethylammoniotetradecyl phosphate 1.48 g (3.42 mmole) of 2-benzyloxy-3-octadecyloxypropanol was dissolved in 12 ml of chloroform freed of ethanol. To the mixture, 1.73 g (17.1 mmole, 4.99 eq) of dry triethylamine was added and then 553 mg (3.61 mmole, 1.05 eq) of phosphorus oxychloride dissolved in 23 ml of chloroform freed of ethanol was added with stirring under ice-cooling. The mixture was stirred at 0° C. for 30 minutes and then at room temperature for 1 hour. The mixture was again cooled on an ice bath and 1.97 g (4.44 mmole, 1.30 eq) of 14-trimethylammoniotetradecylalcohol monotosylate dissolved in 36 ml of dry pyridine was added thereto portionwise. The resulting mixture was stirred at the same temperature for 1 hour and then at room temperature for 43 hours. To the reaction mixture was added 30 ml of an aqueous solution saturated with sodium hydrogencarbonate, and the mixture was concentrated to dryness under reduced pressure. The residue was purified by Amberlite resin (IR-120, 30 ml and IR-410, 15 ml) column chromatography (eluent: 95% tetrahydrofuran). Furthermore, the eluate was concentrated to dryness under reduced pressure and the residue was purified by silica gel (20 g, Merck & Co., Art. 7734; eluent: chloroform:methanol:water=65:25:4) column chromatography to give 1.44 g (yield: 55%) of the above-mentioned compound.

Thin-layer chromatography (silica gel: Merck & Co., Art. 5715, chloroform:methanol:water=65:25:4) Rf=0.42

NMR (90 MHz, CDCl$_3$)δ: 0.87 (3H), 1.26 (54H), 1.53 (4H), 2.77 (2H), 3.19 (9H), 3.30–3.58 (2H), 3.85 (5H), 4.69 (2H), 7.30 (5H)

IR (KBr)cm$^{-1}$: 3420, 2925, 2860, 1640, 1470, 1225, 1095, 1065, 910, 845, 735, 700

EXAMPLE 25

2-(Hydroxy)-3-(octadecyloxy)propyl 14-trimethylammoniotetradecyl phosphate 1.44 g (1.87 mmole) of 2-(benzyloxy)-3-(octadecyloxy)propyl 14-trimethylammoniotetradecyl phosphate was dissolved in 50 ml of 70% acetic acid and 0.5 g of 10% Pd-C was added as a catalyst. The mixture was stirred at room temperature for 4 hours in a hydrogen atmosphere. The reaction mixture was filtered and concentrated to dryness under reduced pressure. Acetone was added to the residue and the solidified substance was collected by filtration, washed with acetone and dried to give 1.24 g (yield: 97.6%) of the above-mentioned compound.

NMR (90 MHz, CDCl$_3$-CD$_3$OD)δ: 0.87 (3H), 1.27 (54H), 1.67 (4H), 3.12 (9H), 3.23–3.52 (4H), 3.81–3.94 (4H), 4.03 (1H)

EXAMPLE 26

2-(Acetoacetoxy)-3-(octadecyloxy)propyl 14-trimethylammoniotetradecyl phosphate 1.20 g (1.77 mmole) of 2-(hydroxy)-3-(octadecyloxy)propyl 14-trimethylammoniotetradecyl phosphate was suspended in a mixture of 25 ml of dry dichloromethane and 25 ml of dry pyridine, and 2 ml of diketene was added to the mixture with stirring at room temperature. The mixture was stirred at room temperature for 3 hours, and concentrated to dryness under reduced pressure. The residue was purified by column chromatography on 20 g of silica gel (Merck & Co., Art. 7734; eluent: chloroform:methanol:water=65:25:4) to give 1.21 g (yield: 89.6%) of the above-mentioned compound. Thin-chromatography (chloroform:methanol:water=65:25:4) Rf=0.42.

NMR (90 MHz, CDCl$_3$:CD$_3$OD)δ: 0.88 (3H), 1.27 (54H), 1.61 (4H), 2.27 (3H), 3.13 (9H), 3.20–3.48 (4H), 3.63 (2H), 3.77–4.02 (4H), 5.20 (1H)

IR (KBr)cm$^{-1}$: 3450, 2925, 2860, 1745, 1720 1635, 1465, 1250, 1070, 835

EXAMPLE 27

2-(Benzyloxy)-3-(octadecyloxy)propyl 8-trimethylammoniooctyl phosphate 2.61 g (6.0 mmole) of 2-benzyloxy-3-octadecyloxypropanol was dissolved in 20 ml of chloroform freed of ethanol, and 3.03 g (30.0 mmole, 5.0 eq) of dry triethylamine was added to the mixture with stirring under ice-cooling. Then, 970 mg (6.3 mmole, 1.05 eq) of phosphorus oxychloride dissolved in 40 ml of chloroform freed of ethanol was added to the mixture. The resulting mixture was stirred at 0° C. for 30 minutes and at room temperature for 1 hour. Then, the mixture was cooled to 0° C. and 2.80 g (7.8 mmole, 1.3 eq) of 8-trimethylammoniooctanol monotosylate suspended in 60 ml of dry pyridine was dropwise added thereto over a period of 20 minutes. The mixture was stirred at 0° C. for 1 hour and at room temperature for 3 days. 50 ml of an aqueous solution saturated with sodium hydrogencarbonate was added the reaction mixture, which was concentrated to dryness under reduced pressure. The residue was purified by column chromatography on Amberlite resin (30 ml of IR-120, 15 ml of IR-410; eluent: 95% tetrahydrofuran).

The eluate was concentrated to dryness and the residue was purified by column chromatography on silica gel (Merck & Co., Art. 7734, 600 g; eluent: chloroform:methanol:water=65:20:1) to give 2.70 g (yield: 66.8%) of the above-mentioned compound.

EXAMPLE 28

2-(Hydroxy)-3-(octadecyloxy)propyl 8-trimethylammoniooctyl phosphate 290 mg (0.43 mmole) of 2-(benzyloxy)-3-(octadecyloxy)propyl 8-trimethylammoniooctyl phosphate was dissolved in 30 ml of 70% acetic acid, and 0.2 g of 10% Pd-C as a catalyst was added to the mixture. The mixture was stirred at room temperature for 4 hours in a hydrogen atmosphere and filtrated. The filtrate was concentrated to dryness under reduced pressure and the residue was purified by silica gel (3 g, Merck & Co., Art. 7734; eluent: chloroform:methanol:water=65:25:4) column chromatography to give 72 mg (yield: 28.7%) of the above-mentioned compound.

EXAMPLE 29

2-(Acetoacetoxy)-3-(octadecyloxy)propyl 8-trimethylammoniooctyl phosphate 72 mg (0.12 mmole) of 2-(hydroxy)-3-(octadecyloxy)propyl 8-trimethylammoniooctyl phosphate was suspended in a mixture of 5 ml of dry dichloromethane and 5 ml of dry pyridine, and 0.5 ml of diketene was added to the mixture with stirring at room temperature. The reaction mixture was stirred at room temperature for 3 hours and then concentrated to dryness under reduced pressure. The residue was purified by silica gel (5 g, Merck & Co., Art. 7734, eluent: chloroform:methanol:water=65:25:4) column chromatography to give 40 mg (yield: 48.6%) of the above-mentioned compound.

Thin-layer chromatography (chloroform:methanol:water=65:25:4) Rf=0.35

NMR (90 MHz, CDCl$_3$-CD$_3$OD)δ: 0.88 (3H), 1.27 (42H), 1.68 (4H), 2.28 (3H), 3.13 (9H), 3.25–3.50 (4H), 3.62 (2H), 3.75–4.03 (4H), 5.21 (1H)

IR (KBr)cm$^{-1}$: 3400, 2930, 2870, 1745, 1725, 1640, 1470, 1225, 1075, 845

EXAMPLE 30

2-(Benzoyloxy)-3-(octadecyloxy)propyl 8-pyridiniooctyl phosphate

By following the procedure of Example 27, 1.76 g (yield: 48.9%) of the above-mentioned compound was obtained from 2.25 g (5.0 mmole) of 2-benzoyloxy-3-octadecyloxypropanol and 2.47 g (6.5 mmole) of 8-pyridiniooctanol monotosylate.

Thin-layer chromatography (developing solvent: chloroform:methanol:water=65:25:4) Rf=0.21

NMR (90 MHz, CDCl$_3$-CD$_3$OD)δ: 0.87 (3H), 1.24 (42H), 1.50 (2H), 1.95 (2H), 3.45 (2H), 3.67–4.17 (4H), 4.61 (2H), 5.38 (1H), 7.43 (3H), 8.05 (4H), 8.43 (1H), 9.01 (2H)

EXAMPLE 31

2-(Hydroxy)-3-(octadecyloxy)propyl 8-pyridiniooctyl phosphate 1.76 g (2.45 mmole) of 2-benzoyloxy derivative synthesized in Example 30 was dissolved in 5 ml of methanol and an aqueous solution containing 11.2 g (4.90 mmole) of 10% tetrabutylammonium hydroxide was added thereto. The mixture was stirred at room temperature for 2 hours and then subjected to the coupled two columns, one containing 40 ml of Amberlite IR-410 and the other 20 ml of Amberlite IR-120 and eluted with 95% hydrous tetrahydrofuran. The eluate was concentrated to dryness and the residue was subjected to column chromatography on 25 g of silica gel. A mixture of chloroform-methanol-water (65:25:4) was used for elution. The desired fraction was concentrated under reduced pressure to give 1.13 g (yield: 75%) of 2-(hydroxy)-3-(octadecyloxy)propyl 8-pyridiniooctyl phosphate as colorless solid.

Silica gel thin-layer chromatography (Merck & Co., Art. 5715)

Rf=0.20 (chloroform:methanol:water=65:25:4)

NMR (90 MHz, CDCl$_3$-CD$_3$OD)δ: 0.87 (3H), 1.24 (42H), 1.50 (2H), 1.96 (2H), 3.35–4.00 (9H), 4.60 (2H), 8.06 (2H), 8.43 (1H), 9.05 (2H)

IR (KBr)cm$^{-1}$: 3350, 2925, 2850, 1635, 1490, 1470, 1230, 1070

EXAMPLE 32

2-(Acetoacetyloxy)-3-(octadecyloxy)propyl 8-pyridiniooctyl phosphate 1.0 g (1.6 mmole) of 2-hydroxy derivative obtained in Example 31 was reacted and treated in the same manner as that of Example 29 to obtain 740 mg (yield: 65%) of the desired product as yellow solid.

Thin-layer chromatography (Merck & Co., Art. 5715) Rf=0.21 (chloroform:methanol:water=65:25:4)

NMR (90 MHz, CDCl$_3$-CD$_3$OD)δ: 0.87 (3H), 1.25 (42H), 1.50 (2H), 1.94 (2H), 2.26 (3H), 3.33-4.03 (8H), 3.70 (2H), 4.61 (2H), 5.18 (1H), 8.06 (2H) 8.44 (1H), 9.06 (2H)

IR (KBr)cm$^{-1}$: 3400, 2920, 2850, 1735, 1715, 1630, 1490, 1465, 1230, 1080, 970

EXAMPLE 33

3-(12-Cyclohexyldodecyloxy)-2-methoxypropyl 10-trimethylammoniodecyl phosphate

By following the procedure of Example 1, 1.5 g (4.2 mmole) of 3-(12-cyclohexyldodecyloxy)-2-methoxypropanol as a starting material was treated to give 1.1 g (yield: 41%) of the desired product.

Thin-layer chromatography (developing solvent: chloroform:methanol:water=65:25:4) Rf=0.16

IR (KBr)cm$^{-1}$: 3430, 2925, 2850, 1465, 1250, 1100, 1075, 1050, 820

NMR (90 MHz, CDCl$_3$)δ: 1.27 (36H), 1.46-1.80 (13H), 3.20 (9H), 3.30-3.90 (14H)

EXAMPLE 34

2-(Benzyloxy)-3-(12-cyclohexyldodecyloxy)propyl 10-trimethylammoniodecyl phosphate By following the procedure of Example 7, 1.0 g (2.31 mmole) of 2-(benzyloxy)-3-(12-cyclohexyldodecyloxy)-propanol was treated to give 0.70 g (yield: 43%) of the desired product.

NMR (90 MHz, CDCl$_3$) δ: 1.15-1.80 (49H), 3.20 (9H), 3.33-4.00 (11H), 4.67 (2H), 7.30 (5H)

EXAMPLE 35

3-(12-Cyclohexyldodecyloxy)-2-hydroxypropyl 10-trimethylammoniodecyl phosphate

By following the procedure of Example 5, 0.70 g of 2-(benzyloxy)-3-(12-cyclohexyldodecyloxy)propyl 10-trimethylammoniodecyl phosphate as a starting material was treated to give 0.60 g (yield: 98%) of the desired product.

NMR (90 MHz, CDCl$_3$)δ: 1.15-1.80 (49H), 3.30 (9H), 3.33-4.00 (11H)

EXAMPLE 36

2-(Acetoacetyloxy)-3-(12-cyclohexyldodecyloxy)propyl 10-trimethylammoniodecyl phosphate By following the procedure of Example 3, 0.60 g of 3-(12-cyclohexyldodecyloxy)-2-hydroxypropyl 10-trimethylammoniodecyl phosphate as a starting material was treated to give 0.58 g (yield: 86%) of the desired product.

Thin-layer chromatography (developing solvent: chloroform:methanol:water=65:25:4) Rf=0.22

IR (KBr)cm$^{-1}$: 3430, 2920, 2855, 1745, 1720, 1465, 1240, 1075, 825

NMR (90 MHz, CDCl$_3$-CD$_3$OD)δ: 1.15-1.90 (49H), 2.25 (3H), 3.13 (9H), 3.23-4.00 (13H), 5.20 (1H)

EXAMPLE 37

1-(15-Methylhexadecyloxy)-2,3-propanediol

To 3.4 g (8.97 mmole) of 3-O-(12-bromododecyl)-1,2-isopropylideneglycerol in 15 ml of anhydrous tetrahydrofuran, isoamylmagnesium bromide (20 mmole) in 15 ml of tetrahydrofuran was added dropwise at 0° C. over a period of 30 minutes in the presence of 0.5 mole percent of dilithium tetrachlorocuprate (Li$_2$CuCl$_4$), and the reaction mixture was stirred at 0° C. for 3 hours. After 0.7 ml of 2N sulfuric acid was added to the mixture to adjust pH to about 2, 30 ml of ethyl acetate was added and the insoluble material was filtered off. The filtrate was washed with water, saturated sodium bicarbonate solution and water, in order, and dried over anhydrous magnesium sulfate. The solvent was distilled off and the residue was subjected to column chromatography on silica gel (100 g) and eluted with hexane-ethyl acetate (20:1) to give 3.0 g of crude 1-O-(15-methylhexadecyl)-2,3-isopropylideneglycerol.

NMR (90 MHz, CDCl$_3$)δ: 0.85 (6H), 1.10-1.85 (33H), 3.33-3.53(4H), 3.60-3.80 (1H), 3.93-4.40 (1H)

The above glycerol derivative (3.0 g) was dissolved in a mixture of 20 ml of methanol and 1 ml of 6N hydrochloric acid and heated under reflux for 4 hours. The solvent was distilled off and water was added to the resulting residue. The insoluble material was collected by filtration, washed with hexane and dried to give 2.50 g (yield: 85%) of the desired product as colorless solid.

NMR (90 MHz, CDCl$_3$)δ: 0.85 (6H), 1.15-1.60 (27H), 2.70 (2H), 3.40-3.94 (7H)

EXAMPLE 38

2-Methoxy-3-(15-methylhexadecyloxy)propanol

By following the procedure of Reference Example 11, 1.7 g (5.15 mmole) of 1-(15-methylhexadecyloxy)-2,3-propanediol was reacted and treated to give 1.46 g (yield: 82%) of the desired product as colorless solid.

NMR (90 MHz, CDCl$_3$)δ: 0.85 (6H), 1.10-1.67 (27H), 2.25 (1H), 3.37-3.80 (7H), 3.47 (3H)

EXAMPLE 39

2-Methoxy-3-(15-methylhexadecyloxy)propyl 10-trimethylammoniodecyl phosphate

By following the procedure of Example 1, 1.20 g (3.49 mmole) of 2-methoxy-3-(15-methylhexadecyloxy)-propanol as a starting material was treated to give 0.86 g (yield: 40%) of the desired product.

Thin-layer chromatography (deveoping solvent: chloroform:methanol:water=65:25:4) Rf=0.16

IR (KBr)cm$^{-1}$: 3400, 2925, 2850, 1465, 1230, 1095, 1065, 840

NMR (90 MHz, CDCl$_3$)δ: 0.85 (6H), 1.15-1.85 (43H), 3.33 (9H), 3.35-3.90 (14H)

EXAMPLE 40

2-(Benzyloxy)-3-(15-methylhexadecyloxy)propanol

A mixture of 2.0 g (6.06 mmole) of 1-(15-methylhexadecyloxy)-2,3-propanediol, 2.54 g (9.09 mmole) of trityl chloride and 20 ml of pyridine was stirred at room temperature for 2 days, and then pyridine was distilled off. To the residue was added 50 ml of ethyl acetate and the ethyl acetate solution was washed with 1N hydrochloric acid, water and saturated sodium bicarbonate solution, in order, and dried over anhydrous magnesium sulfate. The desiccating agent was filtered off and the filtrate was concentrated under reduced pressure. The residue was subjected to column chromatography on silica gel (100 g) and eluted with hexane-ethyl acetate (20:1) to give 2.3 g of crude 1-(trityloxy)-3-(15-methylhexadecyloxy)-2-propanol. This product was treated by following the procedure of that of Reference Example 12 to give 1.0 g (yield: 39%) of the desired product.

NMR (90 MHz, CDCl$_3$)δ: 0.85 (6H), 1.20-1.70 (27H), 2.22 (1H), 3.38-3.78 (7H), 4.67 (2H), 7.33 (5H)

EXAMPLE 41

2-(Benzyloxy)-3-(15-methylhexadecyloxy)propyl 10-trimethylammoniodecyl phosphate By following the procedure of Example 4, 1.0 g (2.4 mmole) of 2-(benzyloxy)-3-(15-methylhexadecyloxy)propanol as a starting material was treated to give 0.70 g (yield: 42%) of the desired product.

NMR (CDCl$_3$)δ: 0.85 (6H), 1.20-1.78 (43H), 3.18 (9H), 3.30-4.00 (11H), 4.69 (2H), 7.32 (5H)

EXAMPLE 42

2-Hydroxy-3-(15-methylhexadecyloxy)propyl 10-trimethylammoniodecyl phosphate

By following the procedure of Example 5, 0.70 g (1.0 mmole) of 2-(benzyloxy)-3-(15-methylhexadecyloxy)propyl 10-trimethylammoniodecyl phosphate as a starting material was treated to give 0.60 g (yield: 98%) of the desired product.

IR (KBr)cm$^{-1}$: 3400, 2930, 2860, 1465, 1205, 1120, 1050

NMR (90 MHz, CDCl$_3$-CD$_3$OD)δ: 0.85 (6H), 1.15-1.90 (43H), 3.17 (9H), 3.25-4.05 (11H)

EXAMPLE 43

2-(Acetoacetyloxy)-3-(15-methylhexadecyloxy)propyl 10-trimethylammoniodecyl phosphate By following the procedure of Example 3, 0.60 g of 2-hydroxy-3-(15-methylhexadecyloxy)propyl 10-trimethylammoniodecyl phosphate as a starting material was treated to give 0.45 g (yield: 66%) of the desired product.

Thin-layer chromatography (developing solvent: chloroform:methanol:water=65:25:4) Rf=0.25

IR (KBr)cm$^{-1}$: 3400, 2925, 2860, 1740, 1715, 1465, 1230, 1070, 840

NMR (90 MHz, CDCl$_3$-CD$_3$OD)δ: 0.85 (6H), 1.15-1.85 (43H), 2.26 (3H), 3.20-4.00 (12H), 5.20 (1H)

EXAMPLE 44

2-Methylcarbamoyloxy-3-octadecyloxypropyl 8-trimethylammoniooctyl phosphate

By following the procedure of 8, 720 mg of the alcohol derivative obtained in Example 28 was reacted with 2 ml of methyl isocyanate to give 320 mg (yield: 41%) of the desired product.

IR (KBr)cm$^{-1}$: 3350 (broad), 2920, 2860, 1720 1465, 1230, 1065

NMR (CDCl$_3$)δ: 0.87 (3H, m), 1.26 (32H, s), 1.13-1.85 (14H, m), 2.83 (3H, d, J=5 Hz), 3.30 (9H, s), 3.20-4.06 (8H, m), 5.08 (1H, m), 8.43 (1H, m)

TLC: Rf=0.15 (CHCl$_3$:MeOH:H$_2$O=65:25:4)

EXAMPLE 45

2-Methylcarbamoyloxy-3-octadecyloxypropyl 14-trimethylammoniotetradecyl phosphate By following the procedure of Example 8, 661 mg of the alcohol derivative obtained in Example 25 was reacted with 2 ml of methyl isocyanate and 1 ml of triethylamine to give 485 mg (yield: 68%) of the desired product.

IR (KBr)cm$^{-1}$: 3400 (broad), 2920, 2860, 1730, 1465, 1250, 1070

NMR(CDCl$_3$)δ: 0.86 (3H, m), 1.25 (32H, s), 1.10-1.73 (26H, m), 2.73 (3H, d, J=5 Hz), 3.31 (9H, s), 3.37-4.03 (8H, m), 4.96 (1H, m), 6.10 (1H, m)

TLC: Rf=0.17 (CHCl$_3$:MeOH:H$_2$O=65:25:4)

EXAMPLE 46

2-(Carboxymethyloxy)-3-(octadecyloxy)propyl 10-trimethylammoniodecyl phosphate

In 120 ml of 80% tetrahydrofuran was dissolved 1.7 g (2.4 mmole) of 2-(2,2-dimethoxy)ethyloxy-3-(octadecyloxy)propyl 10-trimethylammoniodecyl phosphate obtained in Example 22, and 4 ml of Amberlite IR-120[H] was added thereto. The mixture was stirred at 45° C. for 40 hours and then the resin was filtered off. The filtrate was concentrated to dryness under reduced pressure and the residue was dissolved in 200 ml of acetone. To the mixture was added 1 g of activated charcoal powder, and air was introduced into the resulting mixture through a glass tube for 10 hours. Activated charcoal was filtered off and acetone was distilled off. The residue was dissolved in 80% tetrahydrofuran and laid on a column charged with Amberlite 68 (50 ml). The column was washed with 80% tetrahydrofuran, and then elution was conducted with tetrahydrofuran-28% ammonia-methanol (10:1:1). The eluate was concentrated to dryness under reduced pressure, and the residue was dissolved in 80% tetrahydrofuran, laid on a column charged with Amberlite IR-120[H] (10 ml) and eluted with 80% tetrahydrofuran. The eluate was concentrated to dryness under reduced pressure to give 332 mg (yield: 21%) of the desired product.

IR (CHCl$_3$)cm$^{-1}$: 1720, 1230, 1195, 1045, 965

NMR (60 MHz, CDCl$_3$-CD$_3$OD)δ: 0.90 (3H), 1.23-1.80 (48H), 3.13 (9H), 3.27-4.10 (11H), 4.27 (2H)

Effect of the Invention

Referring to Test Examples, the effect of the invention will be described hereinbelow.

TEST EXAMPLE 1

Antitumor action of 2-(acetoacetyloxy)-3-(octadecyloxy)propyl 10-trimethylammoniodecyl phosphate (Example 3)

(i) ICR mice (a group consisting of five mice) were inoculated intraperitoneally with $1 \times 10^5$ Sarcoma 180 cells per mouse, and then given intraperitoneally 0.33 mg/mouse of the compound of Example 3 dissolved in physiological saline, three times in total, 1 hour, 1 day and 2 days after the inoculation. Also, the control compound (III), (IV) or (VI) was given to mice under the same conditions. Shown in Table 1 are the life-span prolongation ratio against the control group not treated with drug (only related to mice of survival days less than 60 days) and the number of survived mice on the 60th day after the initiation of the test.

TABLE 1

| Tested compound | Life-span prolongation ratio (T/C %) | 60th day: No. of survived mice/No. of tested mice |
|---|---|---|
| Compound of Example 3 | 326 | 2/5 |
| Compound III | 162 | 0/5 |
| Compound IV | 109 | 0/5 |
| Compound VI | 202 | 0/5 |
| Control group | 100 | 0/5 |

(ii) When only an amount of the drug was changed to 1 mg/mouse under the above test conditions, the life-span prolongation ratio (T/C %) by the compound of Example 3 was 369, and the number of survived mice on the 60th day was 2 in a group (5 mice). In this case, the compound III for its toxicity gave a smaller life-span prolongation ratio than the control group.

TEST EXAMPLE 2

(i) C3H/He mice (a group consisting of five mice) were inoculated intraperitoneally with $1\times10^4$ MM46 cells per mouse, and each mouse was intraperitoneally given 0.25 mg of drug for consecutive 4 days, starting from the second day after the inoculation. Shown in Table 2 are the life-span prolongation ratio regarding the died mice in the group treated with drug against those in the control group not treated with drug (only related to mice of survival days less than 60 days) and the number of survived mice on the 60th day after the inoculation of MM46.

TABLE 2

| Tested compound | Life-span prolongation ratio (T/C %) | 60th day: No. of survived mice/No. of tested mice |
| --- | --- | --- |
| Compound of Example 3 | 132 | 4/5 |
| Compound III | 155 | 0/5 |
| Control group | 100 | 0/5 |

(ii) In the above test, each mouse was inoculated intraperitoneally with $1\times10^5$ MM46 cells and 0.25 mg of drug was given intraperitoneally to each mouse for consecutive 4 days, starting from the second day after the inoculation. Shown in Table 3 are the life-span prolongation ratio regarding the died mice in the group treated with drug (only related to mice of survival days less than 60 days) and the number of survived mice on 60th day after the inoculation of MM46 cells.

TABLE 3

| Tested compound | Life-span prolongation ratio (T/C %) | 60th day: No. of survived mice/No. of treated mice |
| --- | --- | --- |
| Compound of Example 3 | 125 | 4/5 |
| Control group | 100 | 0/5 |

TEST EXAMPLE 3

Shown in Table 4 is the multiplication-inhibiting effect (IC$_{50}$) of the compound of the present invention against human myelogenous leukemia cells HL-60. The assay was conducted according to the method of R. Gallo et al.: Blood, Vol 54, 713 (1979).

TABLE 4

$$\begin{bmatrix} -OC_{18}H_{37} \\ -OCOCH_2COMe \\ -O\!\!-\!\!\overset{O}{\underset{|}{P}}\!\!-\!\!O(CH_2)_n\overset{+}{N}Me_3 \\ \phantom{-O-P-}O^- \end{bmatrix}$$

| Tested compound | Structure n | Multiplication inhibition against HL - 60 (IC$_{50}$, μg/ml) |
| --- | --- | --- |
| Reference compound 1 | 2 | 6.6 |
| Reference compound 2 | 3 | 11.0 |
| Compound of Example 3 | 10 | 1.5 |

TABLE 4-continued $$\begin{bmatrix} -OC_{18}H_{37} \\ -OCOCH_2COMe \\ -O\!\!-\!\!\overset{O}{\underset{|}{P}}\!\!-\!\!O(CH_2)_n\overset{+}{N}Me_3 \\ \phantom{-O-P-}O^- \end{bmatrix}$$

| Tested compound | Structure n | Multiplication inhibition against HL - 60 (IC$_{50}$, μg/ml) |
| --- | --- | --- |
| Example 3 | | |

TEST EXAMPLE 4

Effect on platelet

Blood was collected from a male rabbit, using a syringe containing 3.15% of citric acid (at a ratio of 1 part to 9 parts of blood) as an anticoagulant, and centrifuged at 1,000 r.p.m. at room temperature for 10 minutes to give platelet rich plasma (PRP). This PRP was further centrifuged at 3,000 r.p.m. for 15 minutes to obtain platelet poor plasma (PPP). By using this PPP, the PRP was diluted and so adjusted as to have a constant platelet concentration (400,000 cells/1 μl). To 250 μl of PRP solution so adjusted was added a certain amount of a test compound solution as prepared beforehand to such a concentration of $10^{-4}$M and a drug concentration in the mixture was adjusted to have a certain level. Platelet aggregation was measured by using a platelet aggregometer (manufactured by Rika Denki Co. in Japan). The results are shown in Table 5 below.

TABLE 5

$$\begin{bmatrix} -OC_{18}H_{37} \\ -OR' \\ -O\!\!-\!\!\overset{O}{\underset{|}{P}}\!\!-\!\!O(CH_2)_n\overset{+}{N}Me_3 \\ \phantom{-O-P-}O^- \end{bmatrix}$$

| Tested compound | Structure R' | n | PAF activity EC$_{50}$ (M) |
| --- | --- | --- | --- |
| Compound of Example 1 | —COCH$_2$COMe | 10 | $>>10^{-4}$ |
| Compound of Example 18 | —CH$_2$COMe | 10 | $>>10^{-4}$ |
| Compound (II) | —COMe | 2 | $3\times10^{-7}>>1\times10^{-7}$ |
| Compound (III) | —Me | 2 | $3\times10^{-5}$ |
| Compound (IV) | —COMe | 2 | $3\times10^{-6}>>3\times10^{-7}$ |
| Compound (V) | —CONMe$_2$ | 2 | $1\times10^{-7}>>3\times10^{-8}$ |

Note:
EC$_{50}$ is a drug concentration causing 50% platelet aggregation.

TEST EXAMPLE 5

Inhibition action against PAF
Inhibition action against PAF in platelet aggregation (Test method and results)

Blood was collected from a male rabbit, using a syringe containing 3.15% of citric acid (at a ratio of 1 part to 9 parts of blood) as an anticoagulant and centrifuged at 1,000 r.p.m. at room temperature for 10 minutes to obtain platelet rich plasma (PRP). This PRP was further centrifuged at 1,400 r.p.m. for 15 minutes to obtain platelet pellet, which was then suspended in Ca$^{++}$-free Tyrode (containing 0.25% of gelatin) to prepare Washed PRP. 250 μl of the Washed PRP was stirred at 37° C. for 2 minutes, and admixed with 25 μl of 0.2–0.5 mM Ca++ solution, followed by stirring for another 30 seconds. Then, a test compound was added to the mixture to a concentration of $3 \times 10^{-5}$M and after further stirring for 2 minutes, $3 \times 10^{-7}$M of PAF was added to the mixture. Platelet aggregation was measured by using a platelet aggregometer (manufactured by Rika Denki Co. in Japan). The activity of the test compound was determined from an inhibition ratio for maximum transmission (i.e. maximum aggregation ratio) by PAF in the control PRP. The results are shown in Table 6 below.

TABLE 6

$$\begin{bmatrix} -OC_{18}H_{37} \\ -OR' \\ -OPO(CH_2)_n\overset{+}{N}Me_3 \\ \quad | \\ \quad O^- \end{bmatrix}$$

| Tested compound | Structure R' | n | Inhibition ratio (%) |
|---|---|---|---|
| Compound of Example 3 | —COCH₂COCH₃ | 10 | 72 |
| Compound of Example 18 | —CH₂COCH₃ | 10 | 100 |
| Reference compound 1 | —COCH₂COCH₃ | 2 | 0 |
| Reference compound 2 | —COCH₂COCH₃ | 3 | 0 |

TEST EXAMPLE 6

The assay was carried out under the same conditions as Test Example 1-i. Shown in Table 7 are the life-span prolongation ratio against the control group not treated with drug (only related to mice of survival days less than 60 days) and the number of survived mice on the 60th day after the initiation of the test.

TABLE 1

| Tested compound (Example No.) | Life-span prolongation ratio (T/C %) | 60th day: No. of survived mice/ No. of tested mice |
|---|---|---|
| 6 | 242 | 0/5 |
| 10 | 212 | 0/5 |
| 11 | 253 | 0/5 |
| 33 | 266 | 0/5 |
| 39 | 265 | 0/5 |
| 43 | 128 | 2/5 |
| 46 | 335 | 0/5 |
| Control group | 100 | 0/5 |

TEST EXAMPLE 7

The assay was carried out under the same conditions as Test Example 2-i. Shown in Table 8 are the life-span prolongation ratio regarding the died mice in the group treated with drug against those in the control group not treated with drug (only related to mice of survival days less than 60 days) and the number of survived mice on the 60th day after the inoculation of MM46.

TABLE 8

| Tested compound (Example No.) | Life-span prolongation ratio (T/C %) | 60th day: No. of survived mice/ No. of tested mice |
|---|---|---|
| 6 | 145 | 4/5 |
| 9 | 170 | 2/5 |
| 10 | 249 | 2/5 |
| 11 | 186 | 2/5 |

TABLE 8-continued

| Tested compound (Example No.) | Life-span prolongation ratio (T/C %) | 60th day: No. of survived mice/ No. of tested mice |
|---|---|---|
| 43 | 232 | 0/5 |
| 46 | 287 | 1/5 |
| Control group | 100 | 0/5 |

TEST EXAMPLE 8

Activity on platelet was assayed under the same conditions as Test Example 4. The results are shown in Table 9.

TABLE 9

| Tested compound (Example No.) | PAF activity $3 \times 10^{-5}$ (M) |
|---|---|
| 6 | 0 |
| 9 | |
| 10 | 0 |
| 11 | 0 |
| 23 | 0 |
| 26 | 0 |
| 29 | 0 |
| 33 | 0 |
| 39 | 0 |
| 43 | 0 |
| 44 | 0 |
| 45 | 0 |
| 46 | 0 |

TEST EXAMPLE 9

Inhibition activity against PAF in platelet aggregation was assayed under the same conditions as Test Example 5. The results are shown in Table 10.

TABLE 10

| Tested Compound (Example No.) | Inhibition ratio (%) |
|---|---|
| 8 | 100 |
| 9 | 55 |
| 10 | 53 |
| 29 | 96 |
| 33 | 100 |
| 39 | 69 |
| 43 | 100 |
| 44 | 100 |

What is claimed is:

1. A compound of the formula:

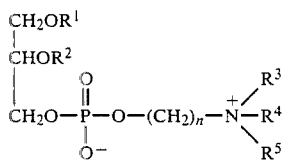

wherein
R¹ is n-octadecyl, 2-oxoeicosyl, octadecylcarbamoyl, 12-cyclohexyldodecyl or 15-methylhexadecyl;
R² is methyl, methylcarbamoyl, methylthiocarbamoyl, acetoacetyl, 2-oxopropyl, formylmethyl or carboxymethyl;
R³, R⁴ and R⁵ are methyl;
n represents an integer of 8 to 14; or a pharmaceutically acceptable salt thereof.

2. A compound according to claim 1, which is 3-(12-cyclohexyldodecyloxy)-2-methoxypropyl 10-trimethylammoniodecyl phosphate.

3. A compound according to claim 1, wherein $R^1$ is n-octadecyl.

4. A compound according to claim 1, wherein $R^2$ is acetoacetyl.

5. A compound according to claim 1, wherein $R^2$ is carboxymethyl.

6. A compound according to claim 1, wherein n is 10.

7. A compound according to claim 1, which is 2-(acetoacetyloxy)-3-(octadecyloxy)propyl 10-trimethylammoniodecyl phosphate.

8. A compound according to claim 1, which is 2-methoxy-3-(2-oxoeicocyloxy)propyl 10-trimethylammoniodecyl phosphate.

9. A compound according to claim 1, which is 2-methylcarbamoyloxy-3-octadecyloxypropyl 10-trimethylammoniodecyl phosphate.

10. A compound according to claim 1, which is 2-methoxy-3-octadecyloxypropyl 10-trimethylammoniodecyl phosphate.

11. A compound according to claim 1, which is 3-octadecylcarbamoyloxy-2-methoxypropyl 10-trimethylammoniodecyl phosphate.

12. A compound according to claim 1, which is 2-(carboxymethyl)-3-(octadecyloxy)propyl 10-trimethylammoniodecyl phosphate.

* * * * *